`US010993899B2`

United States Patent
Blaise et al.

(10) Patent No.: US 10,993,899 B2
(45) Date of Patent: May 4, 2021

(54) COMPOSITION FOR DYEING KERATIN FIBRES, COMPRISING A STYRYL OR NAPHTHYLAMIDE DIRECT DYE BEARING AN AMINOALKYL FUNCTION, DYEING PROCESS AND DYE

(71) Applicant: L'OREAL, Paris (FR)

(72) Inventors: Christian Blaise, Aulnay-sous-bois (FR); Abel Messavussu, Aulnay-sous-bois (FR)

(73) Assignee: L'OREAL, Paris (FR)

( * ) Notice: Subject to any disclaimer, the term of this patent is extended or adjusted under 35 U.S.C. 154(b) by 43 days.

(21) Appl. No.: 16/061,907

(22) PCT Filed: Dec. 16, 2016

(86) PCT No.: PCT/EP2016/081341
§ 371 (c)(1),
(2) Date: Jun. 13, 2018

(87) PCT Pub. No.: WO2017/103045
PCT Pub. Date: Jun. 22, 2017

(65) Prior Publication Data
US 2020/0163855 A1 May 28, 2020

(30) Foreign Application Priority Data

Dec. 18, 2015 (FR) ..................... 1562838

(51) Int. Cl.
*A61Q 5/10* (2006.01)
*A61K 8/49* (2006.01)
*A61Q 5/06* (2006.01)

(52) U.S. Cl.
CPC ........... *A61K 8/4926* (2013.01); *A61Q 5/065* (2013.01); *A61K 2800/30* (2013.01); *A61K 2800/432* (2013.01)

(58) Field of Classification Search
CPC .......... A61Q 5/065; A61K 8/418; A61K 8/49; A61K 8/416; A61K 2800/43; A61K 280/432
USPC ............................................. 8/405
See application file for complete search history.

(56) References Cited

U.S. PATENT DOCUMENTS

| 7,988,741 B2 | 8/2011 | Luukas et al. |
| 2014/0041132 A1* | 2/2014 | Guerin .................. A61K 8/8152 8/405 |

FOREIGN PATENT DOCUMENTS

| CN | 10352117 | * | 1/2014 | .......... C07D 213/38 |
| CN | 103525117 A | | 1/2014 | |
| FR | 2788432 A1 | | 7/2000 | |
| FR | 2912137 A1 | | 8/2008 | |

OTHER PUBLICATIONS

STIC Search Report dated Mar. 17, 2020.*
International Search Report for Application No. PCT/EP2016/081341, dated May 16, 2017/.

* cited by examiner

*Primary Examiner* — Eisa B Elhilo
(74) *Attorney, Agent, or Firm* — The Marbury Law Group, PLLC

(57) ABSTRACT

The invention relates to a process for dyeing and/or lightening keratin fibres using direct dyes of styryl or naphthylamide type bearing a ($C_1$-$C_{18}$)aminoalkyl group. The dyeing process and the composition according to the invention make it possible in particular to obtain long-lasting, intense, chromatic and/or homogeneous colouring on the keratin fibres.

17 Claims, 2 Drawing Sheets

Fig. 1: result of reflectance of TD2 keratin fibres undyed and after dyeing/lightening using compounds 1 to 4 of the invention
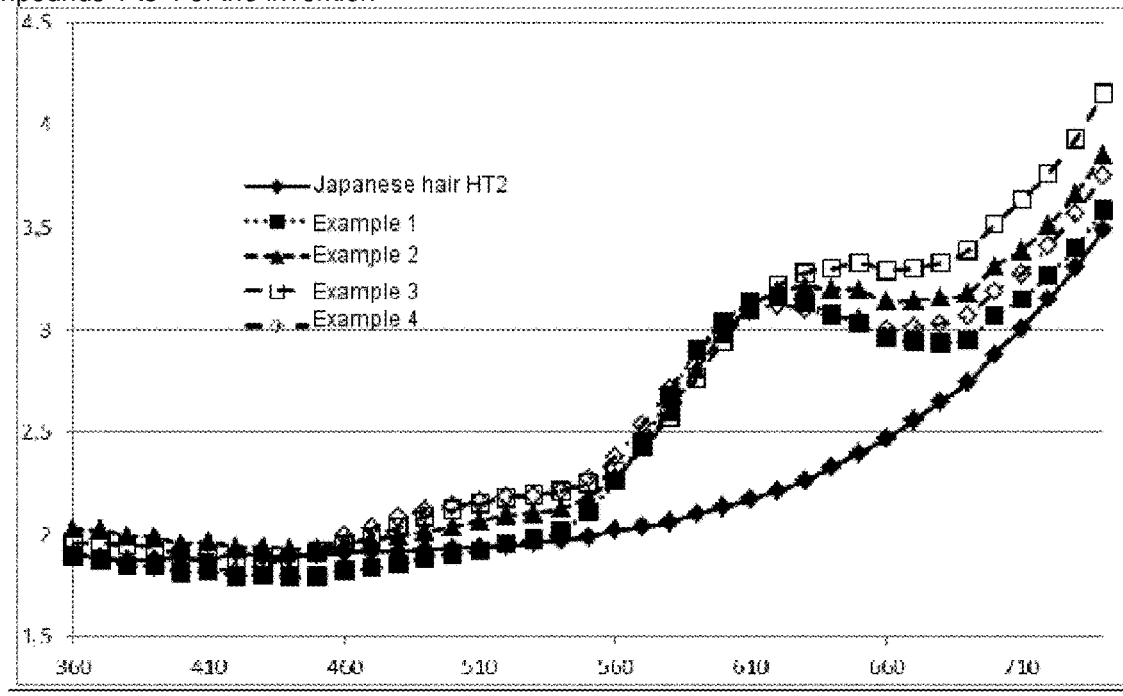
Fig. 2: result of reflectance of TD2 keratin fibres undyed and after dyeing/lightening using compounds 1 to 4 of the invention, followed by 10 successive shampoo washes
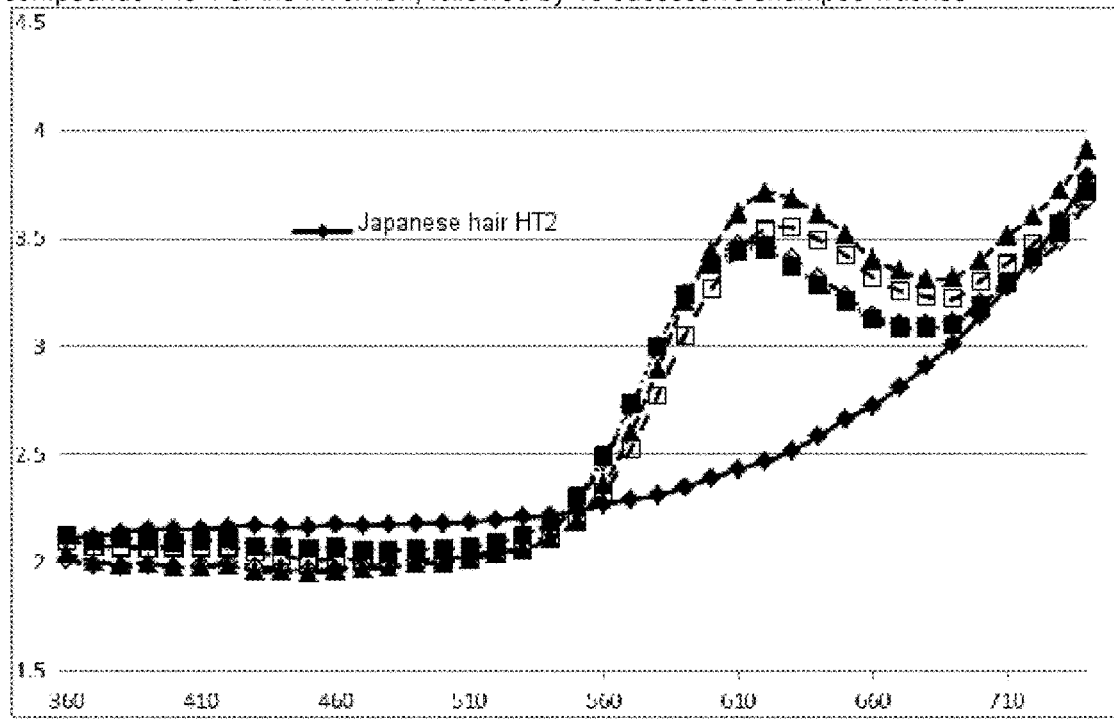

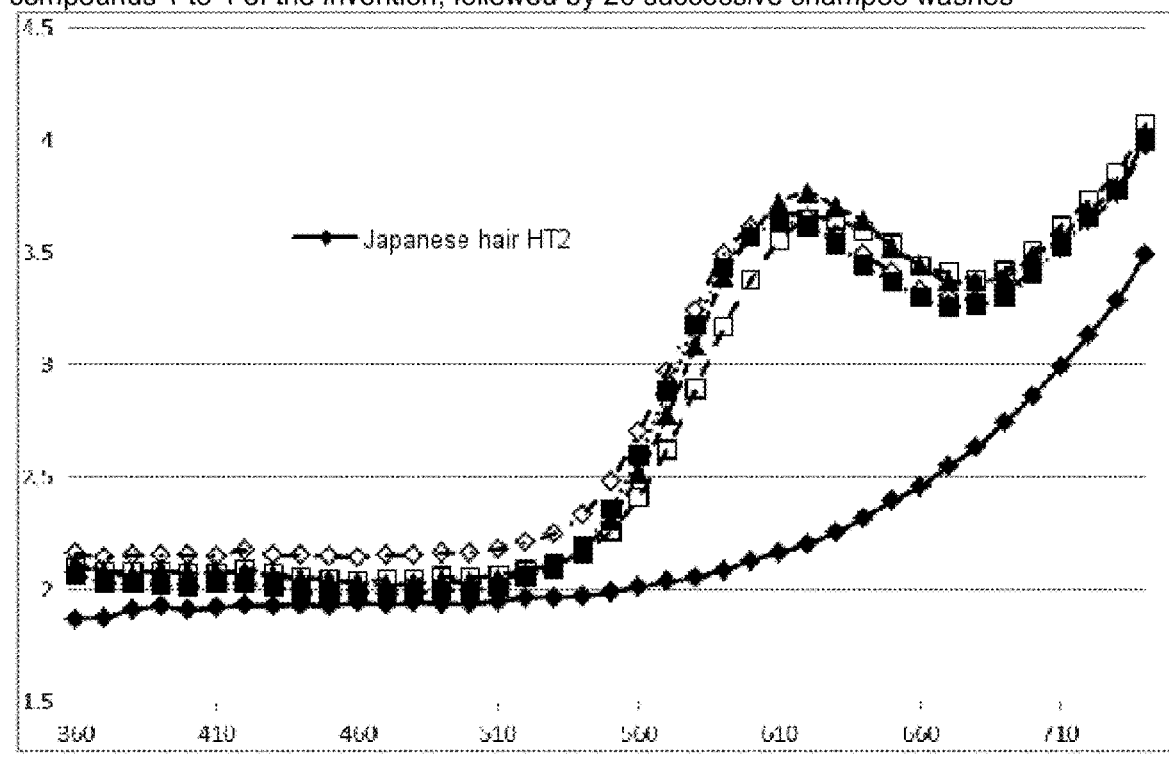
Fig. 3: result of reflectance of TD2 keratin fibres undyed and after dyeing/lightening using compounds 1 to 4 of the invention, followed by 20 successive shampoo washes

COMPOSITION FOR DYEING KERATIN FIBRES, COMPRISING A STYRYL OR NAPHTHYLAMIDE DIRECT DYE BEARING AN AMINOALKYL FUNCTION, DYEING PROCESS AND DYE

CROSS REFERENCE TO RELATED APPLICATIONS

This is a national stage application of PCT/EP2016/081341, filed internationally on Dec. 16, 2016, which claims priority to French Application No. 1562838, filed on Dec. 18, 2015, both of which are incorporated by reference herein in their entireties.

The invention relates to a process for dyeing and/or lightening keratin fibres using direct dyes of styryl or naphthylamide type bearing a ($C_1$-$C_{18}$)aminoalkyl group.

It is known to dye keratin fibres by direct dyeing or semi-permanent dyeing. Direct dyeing or semi-permanent dyeing consists in introducing the colour via a coloured molecule which becomes adsorbed at the surface of the individual hair or which penetrates into the individual hair. Thus, the process conventionally used in direct dyeing consists in applying to the keratin fibres direct dyes, which are coloured and colouring molecules that have affinity for the fibres, in leaving the fibres in contact with the colouring molecules and in then optionally rinsing the fibres. Generally, this technique leads to chromatic colourings.

Scientific research has been conducted for several years to modify the colour of keratin materials, in particular keratin fibres, and in particular to mask white fibres, to modify the colour of the fibres permanently or temporarily, and to satisfy new desires and needs in terms of colours and durability.

The aim of the present invention is to provide novel systems for dyeing the hair, which can, even without the use of a chemical oxidizing and/or reducing agent, produce improved colourings, especially in terms of fastness with respect to external agents, homogeneity of the colouring (little selectivity between the root and the end of the keratin fibres), intensity and chromaticity, and/or which do not impair the cosmetic properties of the keratin fibres. Another aim of the invention is to be able to dye light-coloured keratin fibres efficiently in a chestnut, dark chestnut or even black colour, by mixing the direct dyes.

This aim is achieved with the present invention, a first subject of which is a process for dyeing and/or lightening keratin materials, in particular keratin fibres, preferably human keratin fibres such as the hair, which consists in applying to said materials a cosmetic composition comprising at least one direct dye chosen from those of formulae (I), (IIa) and (IIb) below:

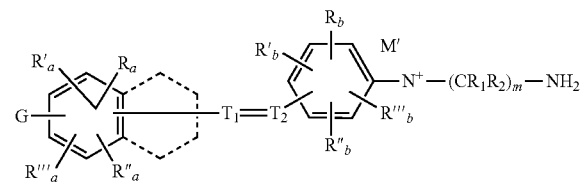
(I)

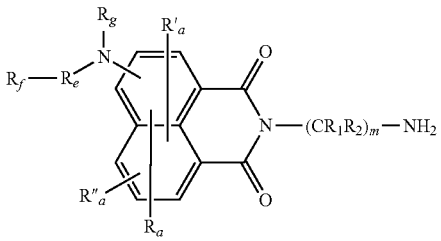
(IIa)

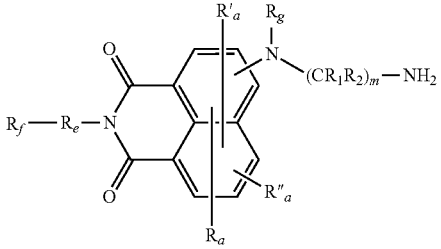
(IIb)

and also the organic or mineral acid or base salts thereof, the optical isomers, geometrical isomers and tautomers thereof, and the solvates thereof such as hydrates; in which formulae (I), (IIa) and (IIb):

$R_1$ and $R_2$, which may be identical or different, represent a hydrogen atom or a $C_1$-$C_6$ alkyl group; preferentially a hydrogen atom;

$T_1$ represents a nitrogen atom or a group $C(R_i)$;

$T_2$ represents a nitrogen atom or a group $C(R_{i'})$;

$R_a$, $R'_a$, $R''_a$, $R'''_a$, $R_b$, $R'_b$, $R''_b$, and $R'''_b$, which may be identical or different, represent a) a hydrogen atom, b) a halogen atom, a group from among: c) amino, d) ($C_1$-$C_4$)alkylamino, e) ($C_1$-$C_4$)dialkylamino, f) cyano, g) carboxy —C(O)OH or carboxylate —C(O)O⁻, Q⁺, h) hydroxy —OH or alkoxide —O⁻Q⁺, i) (poly)halo ($C_1$-$C_6$)alkyl such as trifluoromethyl, j) acylamino, k) ($C_1$-$C_6$)alkoxy, l) ($C_1$-$C_6$)alkylthio, m) (poly)hydroxy ($C_2$-$C_4$)alkoxy, n) ($C_1$-$C_6$)alkylcarbonyloxy, o) ($C_1$-$C_6$)alkoxycarbonyl, p) ($C_1$-$C_6$)alkylcarbonylamino, q) acylamino, r) carbamoyl, s) ($C_1$-$C_6$)alkylsulfonylamino, t) aminosulfonyl, u) —$SO_3H$ or sulfonate —$SO_3^-$, Q⁺ or v) ($C_1$-$C_6$)alkyl optionally substituted with a group chosen from ($C_1$-$C_6$)alkoxy, hydroxyl, cyano, carboxyl, amino, (di)($C_1$-$C_4$)alkylamino, or alternatively the two alkyl radicals borne by the nitrogen atom of the amino group form a 5- to 7-membered heterocycle optionally comprising another nitrogen or non-nitrogen heteroatom; particularly $R_a$, $R'_a$, $R''_a$, $R'''_a$, $R_b$, $R'_b$, $R''_b$, and $R'''_b$ represent a hydrogen or halogen atom or a ($C_1$-$C_4$)alkyl group, preferably a hydrogen atom;

or alternatively two groups $R_a$ and $R'_a$; $R_b$, and $R'_b$ borne by two adjacent carbon atoms together form a benzo or indeno ring, a fused heterocycloalkyl or fused heteroaryl group; the benzo, indeno, heterocycloalkyl or heteroaryl ring being optionally substituted with a halogen atom, an amino, ($C_1$-$C_4$)alkylamino, ($C_1$-$C_4$) dialkylamino, nitro, cyano, carboxyl, hydroxyl or trifluoromethyl group, an acylamino, ($C_1$-$C_4$)alkoxy (poly)hydroxy($C_1$-$C_4$)alkoxy, ($C_1$-$C_4$)alkylcarbonyloxy, ($C_1$-$C_4$)alkoxycarbonyl or ($C_1$-$C_4$)alkylcarbonylamino radical, an acylamino, carbamoyl or alkoxyalkylsulfonylamino radical, an aminosulfonyl radical, or a ($C_1$-$C_6$)alkyl radical optionally substituted with: a group chosen from $(C_1-C_6)$alkoxy, hydroxyl, cyano, carboxyl, amino, $(C_1-C_4)$alkylamino and $(C_1-C_4)$dialkylamino, or alternatively the two alkyl radicals borne by the nitrogen atom of the amino group form a 5- to 7-membered heterocycle optionally comprising another nitrogen or non-nitrogen heteroatom; preferentially, $R_a$ and $R'_a$ together form a benzo group;

or alternatively when $T_1$ represents $CR_i$, two groups $R_i$ and $R_a$; and/or when $T_2$ represents a group, R', and $R'_a$ together form a fused (hetero)cycloalkyl, preferentially cycloalkyl such as cyclohexyl;

$R_g$ represents a hydrogen atom, a (hetero)aryl$(C_1-C_4)$ alkyl group or a $(C_1-C_6)$alkyl group that is optionally substituted; preferentially, $R_b$ represents a hydrogen atom or a $(C_1-C_3)$alkyl or benzyl group;

$R_e$ represents a covalent bond, a linear or branched, optionally substituted $(C_1-C_8)$alkylene or $(C_2-C_8)$alkenylene hydrocarbon-based chain, preferably R. represents an unsubstituted $(C_1-C_6)$alkylene;

$R_f$ represents a hydrogen atom, a $(C_1-C_4)$alkoxy group, an amino group $R_3R_4N-$, a quaternary ammonium group M', $R_3R_4R_5N^+-$ in which $R_3$, $R_4$ and $R_5$, which may be identical or different, represent a hydrogen atom or a $(C_1-C_4)$ alkyl group or $R_3R_4N$-represents an optionally substituted heteroaryl group, preferentially an optionally substituted imidazolyl group, or alternatively M', $R_3R_4R_5N^+-$ represents an optionally substituted cationic heteroaryl group, preferentially an imidazolinium group optionally substituted with a $(C_1-C_3)$alkyl group;

G represents a group i) $-NR_cR_d$, ii) $-OR$ with R representing a) a hydrogen atom, b) an optionally substituted, preferentially unsubstituted $(C_1-C_6)$alkyl group, c) an optionally substituted (hetero)aryl group, d) an optionally substituted (hetero)aryl$(C_1-C_6)$alkyl group such as benzyl, e) optionally substituted (hetero)cycloalkyl group, f) optionally substituted (hetero)cycloalkyl$(C_1-C_6)$alkyl group; according to a particular embodiment, G represents a group $-NR_cR_d$, according to another particular embodiment, G represents a $(C_1-C_6)$alkoxy group; or alternatively when G represents $-NR_cR_d$, two groups $R_c$ and $R'_a$ and/or $R_d$ and $R_a$ together form a saturated heteroaryl or heterocycle, optionally substituted with one or more $(C_1-C_6)$alkyl groups, preferentially a 5- to 7-membered heterocycle containing one or two heteroatoms chosen from nitrogen and oxygen; more preferentially, the heterocycle is chosen from morpholinyl, piperazinyl, piperidyl and pyrrolidinyl groups;

$R_c$ and $R_d$, which may be identical or different, represent a hydrogen atom or a group from among: a) optionally substituted (hetero)aryl such as phenyl, b) optionally substituted (hetero)aryl$(C_1-C_4)$alkyl, c) optionally substituted (hetero)cycloalkyl, d) optionally substituted (hetero)cycloalkyl$(C_1-C_4)$alkyl or f) optionally substituted $(C_1-C_8)$alkyl;

or alternatively two adjacent radicals $R_c$ and $R_d$ borne by the same nitrogen atom together form an optionally substituted heterocyclic or optionally substituted heteroaryl group;

$R_i$ and $R'_i$, which may be identical or different, represent a hydrogen atom or a $(C_1-C_4)$alkyl group;

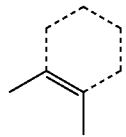

represents a (hetero)aryl group fused to the phenyl ring; or alternatively is absent from the phenyl; preferentially, when the ring is present, the ring is a benzo;

m represents an integer between 1 and 18 inclusive, particularly an integer between 1 and 14 inclusive; preferentially an integer between 2 and 10 inclusive; more preferentially an integer between 3 and 8; more particularly an integer between 4 and 6;

M' represents an anionic counterion, derived from a salt of an organic or mineral acid, or from an organic or mineral base that ensures the electrical neutrality of the molecule;

$Q^+$ represents a cationic counterion, derived from a salt of an organic or mineral acid, or from an organic or mineral base that ensures the electrical neutrality of the molecule such as alkali metal, alkaline-earth metal or ammonium;

it being understood that when the molecule comprises a carboxylate, sulfonate or alkoxide group, then M' and $Q^+$ may be absent to ensure the electrical neutrality of said molecule.

Another subject of the invention is novel dyes chosen from those of formulae (I''''a) and (I''''b) below:

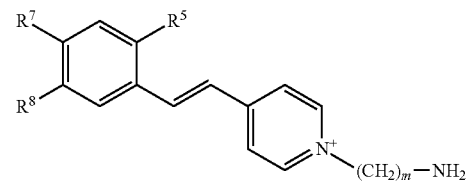

(I''''a)

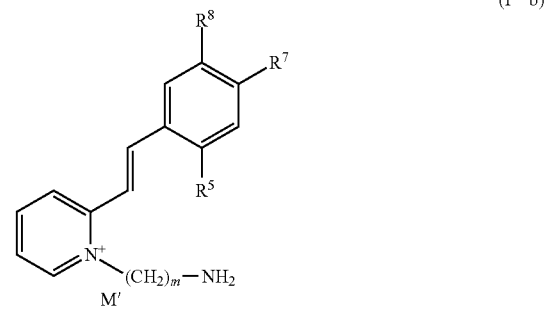

(I''''b)

and also the organic or mineral acid or base salts thereof, the optical isomers, geometrical isomers and tautomers thereof, and the solvates thereof such as hydrates; in which formulae (I''''a) and (I''''b) $R^5$, $R^7$, $R^8$ and m are as defined below for (I'''a) and (I'''b).

Another subject of the invention is a cosmetic composition comprising at least one direct dye chosen from those of formulae (I'''a), (I'''b), (IIa) and (IIb) as defined previously.

Another subject of the invention is the use of at least one direct dye chosen from those of formulae (I), (IIa) and (IIb) as defined previously, for dyeing and/or lightening dark keratin materials, in particular keratin fibres with a tone depth of less than or equal to 6, preferably less than or equal to 4.

The colourings obtained are aesthetic, strong, chromatic and fast with respect to common attacking factors such as sunlight, perspiration, sebum and other hair treatments such as successive shampooing, while at the same time being gentle on the keratin fibres. The intensity obtained is noteworthy. This is likewise the case for the homogeneity of the colour from the root to the end of the keratin fibres.

The process and the composition of the invention make it possible to obtain, with the fluorescent dyes of the invention, lightening of dark keratin materials. In particular, the process of the invention makes it possible to obtain lightening of keratin fibres such as the hair, which lightening is very fast with respect to shampooing, common attacking factors (sunlight, perspiration) and other hair treatments without degrading the keratin fibre.

BRIEF DESCRIPTION OF THE DRAWINGS

FIG. 1 is a graph showing the result of reflectance of TD2 keratin fibres undyed and after dyeing/lightening using compounds 1 to 4 of the invention.

FIG. 2 is a graph showing the result of reflectance of TD2 keratin fibres undyed and after dyeing/lightening using compounds 1 to 4 of the invention, followed by 10 successive shampoo washes.

FIG. 3 is a graph showing the result of reflectance of TD2 keratin fibres undyed and after dyeing/lightening using compounds 1 to 4 of the invention, followed by 20 successive shampoo washes.

For the purposes of the invention, the term "dark keratin material" means a keratin material that has a numerical luminescence L* in the CIE system L*a*b*, of less than or equal to 45 and preferably less than or equal to 40, given that, moreover, L*=0 is equivalent to black and L*=100 is equivalent to white.

For the purposes of the invention, the term "dark hair" means hair with a tone depth of less than or equal to 6 (dark blond) and preferably less than or equal to 4 (chestnut-brown).

The lightening of hair is evaluated by the "tone depth", which characterizes the degree or level of lightening. The notion of "tone" is based on the classification of natural shades, one tone separating each shade from the shade immediately following or preceding it. This definition and the classification of natural shades are well known to hair-styling professionals and are published in the book "Sciences des traitements capillaires [Hair treatment sciences]" by Charles Zviak, 1988, published by Masson, pages 215 and 278.

The tone depths range from 1 (black) to 10 (very light blond), one unit corresponding to one tone; the higher the figure, the lighter the shade.

An artificially dyed keratin fibre is a fibre whose colour has been modified by a dyeing treatment, for example dyeing with direct dyes or oxidation dyes.

The lightening properties of the composition of the invention after application to dark keratin fibres, for example chestnut-brown fibres, may be achieved by reflectance:
  the fibres are irradiated with visible light in the wavelength range from 400 to 700 nanometres;
  the curves of reflectance as a function of the wavelength, for fibres treated with the composition of the invention and for untreated fibres, are then compared;
  the curve corresponding to the treated fibres should show a reflectance in the wavelength range from 450 to 700 nanometres higher than the curve corresponding to the untreated fibres.

This means that, in the wavelength range from 450 to 700 nanometres, there is at least one region in which the reflectance curve corresponding to the treated fibres is higher than the reflectance curve corresponding to the untreated fibres. The term "higher" means a difference in reflectance of at least 0.05% and preferably of at least 0.1%. This does not prevent there from being in the wavelength range from 450 to 700 nanometres at least one region in which the reflectance curve corresponding to the treated fibres is superposable, or lower than the reflectance curve corresponding to the untreated hair.

Preferably, the wavelength at which the difference is maximal between the reflectance curve for the treated hair and that for the untreated hair is in the wavelength range from 450 to 650 nanometres and preferably in the wavelength range from 450 to 620 nanometres.

For the purposes of the present invention and unless otherwise indicated:
  the dyes according to the invention are capable of absorbing light at a wavelength $\lambda_{abs}$ particularly of between 400 and 700 nm inclusive;
  the "fluorescent" dyes according to the invention are styryl dyes of formula (I), i.e. in which $T_1$ and $T_2$ represent a group $CR_i$ and $CR_{i'}$, preferably CH, or of formula (IIa) or (IIb) which are capable of absorbing light in the visible range at a wavelength $\lambda_{abs}$ particularly between 400 and 800 nm and of re-emitting in the visible range at a longer wavelength $\lambda_{em}$ than that absorbed of between 400 and 800 nm; the difference between the absorption wavelength and the emission wavelength, also known as the Stoke's shift, is between 1 nm and 100 nm. More preferentially, fluorescent dyes are dyes that are capable of absorbing at a wavelength $\lambda_{abs}$ of between 420 and 550 nm and of re-emitting in the visible range at a wavelength $\lambda_{em}$ of between 470 and 600 nm;
  the "blue" dyes according to the invention are dyes that absorb light in the visible spectrum and which appear blue visually, i.e. which absorb light at an absorption wavelength Amax greater than 550 nm and less than or equal to 700 nm, in particular between 560 nm and 700 nm, preferably between 580 and 650 nm these dyes are preferably direct dyes, and may be cationic or non-cationic, and are preferably cationic;
  an "alkylene chain" represents a $C_1$-$C_8$ divalent acyclic hydrocarbon-based chain; particularly $C_1$-$C_6$, more particularly linear $C_1$-$C_4$; optionally substituted with one or more groups, which may be identical or different, chosen from i) hydroxyl, ii) ($C_1$-$C_2$)alkoxy, iii) (poly)hydroxy($C_2$-$C_4$)alkoxy(di)($C_1$-$C_2$)(alkyl)amino, iv) $R^a$—$Z^a$—C($Z^b$)—$Z^c$, and v) $R^a$—$Z^a$—S(O)$_t$$Z^c$— with $Z^a$ and $Z^b$, which may be identical or different, representing an oxygen or sulfur atom, or a group $NR^{a'}$, $Z^c$, representing a bond, an oxygen or sulfur atom, or a group $NR^a$; $R^a$, representing an alkali metal, a hydrogen atom, an alkyl group, or alternatively is absent if another part of the cationic molecule, and $R^{a'}$ representing a hydrogen atom or an alkyl group, and t is equal to 1 or 2; more particularly, the groups iv) are chosen from carboxylate —C(O)—O⁻ and —C(O)—O⁻, Q⁺ with Q⁺ as defined previously, carboxyl —C(O)—OH, guanidino $H_2$H—C($NH_2$)—N(H)—, amidino $H_2$H—C($NH_2$)—, (thio)ureo $H_2$N—C(O)—N(H)— and $H_2$N—C(S)—N(H)—, aminocarbonyl —C(O)—NRa'$_2$ or aminothiocarbonyl —C(S)—NRa'$_2$; carbamoyl Ra'—C(O)—NRa'- or thiocarbamoyl Ra'—

C(S)—N(Ra')- with Ra', which may be identical or different, representing a hydrogen atom or a ($C_1$-$C_4$) alkyl group;

the "aryl" or "heteroaryl" radicals or the aryl or heteroaryl part of a radical may be substituted with at least one substituent borne by a carbon atom, chosen from:

a $C_1$-$C_{16}$ and preferably $C_1$-$C_8$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;

a halogen atom;

a hydroxyl group;

a $C_1$-$C_2$ alkoxy radical;

a (poly)hydroxy($C_2$-$C_4$)alkoxy radical;

an amino radical;

a 5- or 6-membered heterocycloalkyl radical;

an optionally cationic 5- or 6-membered heteroaryl radical, preferentially imidazolium, optionally substituted with a ($C_1$-$C_4$)alkyl radical, preferentially methyl;

an amino radical substituted with one or two identical or different $C_1$-$C_6$ alkyl radicals, optionally bearing at least:

i) a hydroxyl group, ii) an amino group optionally substituted with one or two optionally substituted $C_1$-$C_3$ alkyl radicals, said alkyl radicals possibly forming with the nitrogen atom to which they are attached a saturated or unsaturated, optionally substituted 5- to 7-membered heterocycle, optionally comprising at least one other nitrogen or non-nitrogen heteroatom, iii) a quaternary ammonium group —N$^+$R'R"R''', M$^-$ for which R', R" and R''', which may be identical or different, represent a hydrogen atom or a $C_1$-$C_4$ alkyl group; and M$^-$ represents the counterion of the organic or mineral acid or of the corresponding halide, or iv) an optionally cationic 5- or 6-membered heteroaryl radical, preferentially imidazolium, optionally substituted with a ($C_1$-$C_4$)alkyl radical, preferentially methyl;

an acylamino radical (—NR—C(O)—R') in which the radical R is a hydrogen atom or a $C_1$-$C_4$ alkyl radical optionally bearing at least one hydroxyl group and the radical R' is a $C_1$-$C_2$ alkyl radical;

a carbamoyl radical ((R)$_2$N—C(O)—) in which the radicals R, which may be identical or different, represent a hydrogen atom or a $C_1$-$C_4$ alkyl radical optionally bearing at least one hydroxyl group;

an alkylsulfonylamino radical (R'—S(O)$_2$—N(R)—) in which the radical R represents a hydrogen atom or a $C_1$-$C_4$ alkyl radical optionally bearing at least one hydroxyl group and the radical R' represents a $C_1$-$C_4$ alkyl radical, or a phenyl radical;

an aminosulfonyl radical ((R)$_2$N—S(O)$_2$—) in which the radicals R, which may be identical or different, represent a hydrogen atom or a $C_1$-$C_4$ alkyl radical optionally bearing at least one hydroxyl group;

a carboxyl radical in the acid or salified form (preferably salified with an alkali metal or a substituted or unsubstituted ammonium);

a cyano group;

a nitro or nitroso group;

a polyhaloalkyl group, preferably trifluoromethyl;

the cyclic or heterocyclic part of a non-aromatic radical may be substituted with at least one substituent chosen from the following groups:

hydroxyl;

$C_1$-$C_4$ alkoxy, $C_2$-$C_4$ (poly)hydroxyalkoxy;

$C_1$-$C_4$ alkyl;

alkylcarbonylamino (R—C(O)—N(R')—) in which the radical R' is a hydrogen atom or a $C_1$-$C_4$ alkyl radical optionally bearing at least one hydroxyl group, and the radical R is a $C_1$-$C_2$ alkyl radical or an amino radical optionally substituted with one or two $C_1$-$C_4$ alkyl groups, which may be identical or different, themselves optionally bearing at least one hydroxyl group, said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;

alkylcarbonyloxy (R—C(O)—O—) in which the radical R is a $C_1$-$C_4$ alkyl radical or an amino group optionally substituted with one or two identical or different $C_1$-$C_4$ alkyl groups themselves optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

alkoxycarbonyl (R—X—C(O)—) in which the radical R is a $C_1$-$C_4$ alkoxy radical, X is an oxygen atom or an amino group optionally substituted with a $C_1$-$C_4$ alkyl group itself optionally bearing at least one hydroxyl group, said alkyl radical possibly forming with the nitrogen atom to which it is attached a saturated or unsaturated, optionally substituted 5- to 7-membered heterocycle, optionally comprising at least one other nitrogen or non-nitrogen heteroatom;

a cyclic or heterocyclic radical, or a non-aromatic part of an aryl or heteroaryl radical, which may also be substituted with one or more oxo groups;

a hydrocarbon-based chain is unsaturated when it comprises one or more double bonds and/or one or more triple bonds;

an "aryl" radical represents a monocyclic or fused or non-fused polycyclic carbon-based group containing from 6 to 22 carbon atoms, at least one ring of which is aromatic;

preferentially, the aryl radical is a phenyl, biphenyl, naphthyl, indenyl, anthracenyl or tetrahydronaphthyl;

a "heteroaryl radical" represents an optionally cationic, 5- to 22-membered, monocyclic or fused or non-fused polycyclic group, comprising from 1 to 6 heteroatoms chosen from nitrogen, oxygen, sulfur and selenium, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthyl and the ammonium salt thereof;

a "heterocyclic radical" or is a radical which may contain one or two unsaturations, but is a monocyclic or fused or non-fused polycyclic, 5- to 22-membered non-aromatic radical comprising from 1 to 6 heteroatoms chosen from nitrogen, oxygen, sulfur and selenium;

a "heterocycloalkyl radical" is a heterocyclic radical comprising at least one saturated ring;

an "alky/radical" is a linear or branched $C_1$-$C_{10}$ and preferably $C_1$-$C_4$ hydrocarbon-based radical;

an "alkenylene radical" is an unsaturated hydrocarbon-based divalent radical as defined previously, which may contain from 1 to 4 conjugated or unconjugated double bonds —C=C—; the alkenylene group particularly contains 1 or 2 unsaturations;

the term "optionally substituted" attributed to the alkyl radical implies that said alkyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, said alkyl radicals possibly forming with the nitrogen atom that bears them a 5- to 7-membered heterocycle optionally comprising another heteroatom identical to or different from nitrogen; v) or a quaternary ammonium group —$N^+R'R''R'''$, $M^-$ for which R', R" and R'", which may be identical or different, represent a hydrogen atom or a $C_1$-$C_4$ alkyl group, or alternatively —$N^+R'R''R'''$ forms a heteroaryl such as imidazolium optionally substituted with a $C_1$-$C_4$ alkyl group, and $M^-$ represents the counterion of the organic or mineral acid or of the corresponding halide;

an "alkoxy radical" is an alkyl-oxy radical for which the alkyl radical is a linear or branched $C_1$-$C_8$ and preferentially $C_1$-$C_6$ hydrocarbon-based radical;

when the alkoxy group is optionally substituted, this implies that the alkyl group is optionally substituted as defined above;

the "tone depth" is the unit known to hairstyling professionals, and published in the book "Science des traitements capillaires [Hair treatment sciences]" by Charles Zviak, 1988, published by Masson, pages 215 and 278; the tone depths range from 1 (black) to 10 (very light blond), one unit corresponding to one tone, the higher the figure, the lighter the shade;

a "dark" keratin fibre is a keratin fibre whose lightness L* measured in the CIE L*a*b* system is less than or equal to 45 and preferably less than or equal to 40, given moreover that L*=0 is equivalent to black and L*=100 is equivalent to white;

"naturally or artificially dark hair" means hair whose tone depth is less than or equal to 6 (dark blond) and preferably less than or equal to 4 (chestnut-brown). Artificially dyed hair is hair whose colour has been modified by a dye treatment, for example dyeing with direct dyes or oxidation dyes;

the term "organic or mineral acid salt" more particularly means the salts chosen from a salt derived from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)—OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)$—OH; xiv) triflic acid $CF_3SO_3H$; and xv) tetrafluoroboric acid $HBF_4$;

the term "anionic counterion" means an anion or an anionic group derived from an organic or mineral acid which counterbalances the cationic charge of the dye; more particularly, the anionic counterion is chosen from: i) halides such as chloride or bromide; ii) nitrates; iii) sulfonates, including $C_1$-$C_6$ alkylsulfonates: Alk-S(O)$_2$O$^-$ such as methanesulfonate or mesylate and ethanesulfonate; iv) arylsulfonates: Ar—S(O)$_2$O$^-$ such as benzenesulfonate and toluenesulfonate or tosylate; v) carboxylates Alk-C(O)—OH with Alk representing a ($C_1$-$C_6$)alkyl group optionally substituted with one or more hydroxyl or carboxylate groups such as citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$, xiii) phosphates O=P(OH)$_2$—O$^-$, O=P(O$^-$)$_2$—OH O=P(O$^-$)$_3$, HO—[P(O)(O$^-$)]W—P(O)(O$^-$)$_2$ with w being an integer; xiv) acetate; xv) triflate; and xvi) borates such as tetrafluoroborate, xvii) disulfate (O=)$_2$S(O$^-$)$_2$ or $SO_4^{2-}$ and monosulfate $HSO_4^-$, the anionic counterion, derived from the organic or mineral acid salt, ensures the electrical neutrality of the molecule; thus, it is understood that when the anion comprises several anionic charges, then the same anion may serve for the electrical neutrality of several cationic groups in the same molecule or else may serve for the electrical neutrality of several molecules; for example, a dye of formula (I), (IIa) or (IIb) which contains two cationic groups may contain either two "singly charged" anionic counterions or a "doubly charged" anionic counterion such as (O=)$_2$S(O$^-$)$_2$ or O=P(O$^-$)$_2$—OH;

moreover, the addition salts that may be used in the context of the invention are especially chosen from salts of addition with a cosmetically acceptable base such as basifying agents as defined below, for instance alkali metal hydroxides, such as sodium hydroxide or potassium hydroxide, aqueous ammonia, amines or alkanolamines;

the expression "at least one" is equivalent to "one or more"; and the expression "inclusive" for a range of concentrations means that the limits of the range are included in the defined range.

The Composition of the Invention

The composition according to the invention is a cosmetic composition, i.e. it is in a cosmetic medium and comprises at least one direct dye chosen from those of formulae (I), (IIa) and (IIb) as defined previously.

According to a particular embodiment of the invention, the cosmetic composition comprises one or more direct dyes of formula (I), (IIa) or (IIb) as defined previously and one or more blue dyes, in particular direct dyes, preferably cationic dyes.

Preferentially, the cosmetic composition of the invention does not comprise any dyes other than the direct dyes of formula (I), (IIa) or (IIb) as defined previously and the blue dyes as defined previously.

The Cosmetic Medium:

The term "cosmetic medium" means a medium that is suitable for dyeing keratin fibres, also known as a dye support, which is a cosmetic medium generally formed from water or a mixture of water and one or more organic solvents or a mixture of organic solvents. Preferably, the composition comprises water and in a content especially of between 5% and 95% inclusive relative to the total weight of the composition.

The term "organic solvent" means an organic substance capable of dissolving another substance without chemically modifying it.

The Organic Solvents:

Mention may be made, as organic solvent, for example, of lower $C_1$-$C_4$ alkanols, such as ethanol and isopropanol, polyols and polyol ethers, such as 2-butoxyethanol, propylene glycol, propylene glycol monomethyl ether, diethylene glycol monoethyl ether and diethylene glycol monomethyl ether, and also aromatic alcohols, such as benzyl alcohol or phenoxyethanol, and mixtures thereof.

The organic solvents are preferably present in proportions preferably of between 0.1% and 40% by weight inclusive relative to the total weight of the dye composition, more preferably between 1% and 30% by weight approximately and even more preferably of between 5% and 25% by weight inclusive relative to the total weight of the composition.

Direct Dyes of the Invention:

According to one embodiment, the dye(s) of the invention are of formula (I). Preferably, the direct dye(s) of the invention are chosen from the styryl dyes of formula (I') below:

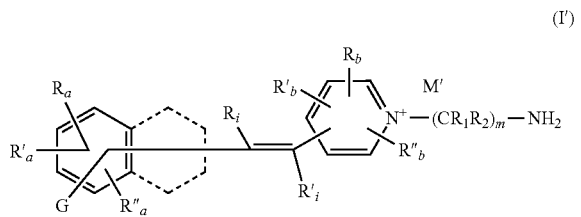

and also the organic or mineral acid or base salts thereof, the optical isomers, geometrical isomers and tautomers thereof, and the solvates thereof such as hydrates; in which formula (I') G, $R_a$, $R'_a$, $R''_a$, $R_b$, $R'_b$, $R''_b$, $R_i$, $R'_i$, $R_1$, $R_2$ and m are as defined previously for (I).

In particular, the dye(s) of the invention are chosen from those of formula (I') for which:

$R_1$ and $R_2$, which may be identical or different, represent a hydrogen atom;

$R_i$ and $R'_i$, which may be identical or different, represent a hydrogen atom or a ($C_1$-$C_4$)alkyl group, preferably hydrogen;

$R_a$, $R'_a$ and $R''_a$, which may be identical or different, represent a hydrogen atom, a halogen atom such as fluorine, or an —OH, —$O^-Q^+$, ($C_1$-$C_6$)alkoxy, nitro, or cyano group, with $Q^+$ as defined previously;

$R_b$, $R'_b$, and $R''_b$, which may be identical or different, represent a hydrogen atom or a ($C_1$-$C_6$)alkyl group;

or alternatively two contiguous radicals $R_b$ and $R'_b$ form, together with the carbon atoms that bear them, a benzo group that is fused to the pyridinium group, said benzo group possibly being substituted; preferably, said benzo group is unsubstituted;

G represents a group —$NR_cR_d$ or ($C_1$-$C_6$)alkoxy group which is optionally substituted, preferentially unsubstituted; according to a particular embodiment, G represents a group —$NR_cR_d$, according to another particular embodiment, G represents a ($C_1$-$C_6$)alkoxy group;

$R_i$ and $R'_i$, which may be identical or different, represent a hydrogen atom or a ($C_1$-$C_4$)alkyl group;

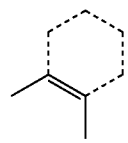

represents an aryl or heteroaryl group fused to the phenyl ring; or alternatively is absent from the phenyl ring; preferentially, when the ring is present, the ring is a benzo;

m represents an integer between 1 and 18 inclusive, particularly an integer between 2 and 16 inclusive; preferentially an integer between 3 and 10; more preferentially an integer between 4 and 6;

$R_c$ and $R_d$, which may be identical or different, represent a hydrogen atom, a ($C_1$-$C_8$)alkyl group optionally substituted in particular with one or more groups chosen from i) cyano, ii) ($C_1$-$C_3$)alkoxy, iii) hydroxyl and iv) ($C_1$-$C_3$)alkylcarbonyl, preferably with one or more hydroxyl groups; and M' represents an anionic counterion, derived from a salt of an organic or mineral acid, or from an organic or mineral base that ensures the electrical neutrality of the molecule; it being understood that when the molecule comprises an alkoxide group, then M' and $Q^+$ may be absent to ensure the electrical neutrality of said molecule.

Preferably, the direct dye(s) of the invention are chosen from the styryl dyes of formula (I") below:

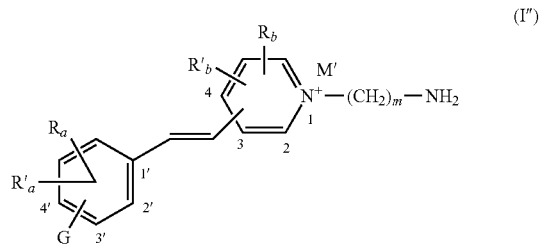

and also the organic or mineral acid salts thereof, the optical isomers, geometrical isomers and tautomers thereof, and the solvates thereof such as hydrates;

in which formula (I") G, $R_a$, $R'_a$, $R_b$, $R'_b$ and m are as defined previously.

According to a particular embodiment, the group G is in the para position relative to the —CH═CH— group, i.e. in position 4' of the phenyl group. According to another particular embodiment, the group G is in the ortho position relative to the —CH═CH— group, i.e. in position 2' of the phenyl group. According to one embodiment, the —CH═CH— group is in the para position of the pyridinium group, i.e. in position 4.

According to another advantageous variant, the —CH═CH— group is in the ortho position of the pyridinium group, i.e. in position 2.

According to a preferred embodiment of the invention, the dyes of the invention are chosen from the compounds of formulae (I'''a) and (I'''b) below:

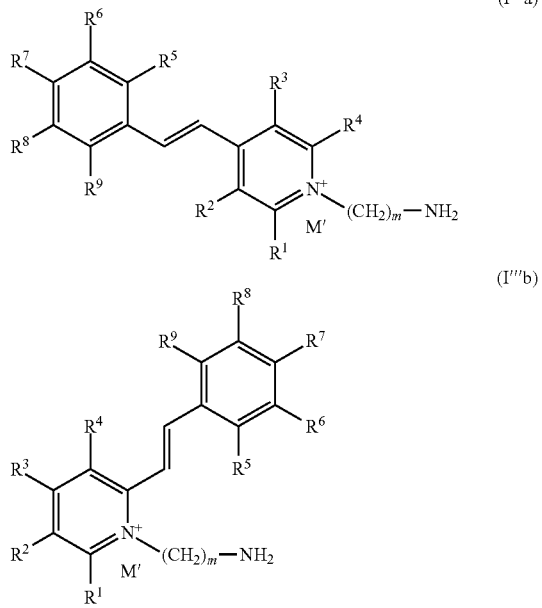

and also the organic or mineral acid salts thereof, the optical isomers, geometrical isomers and tautomers thereof, and the solvates thereof such as hydrates;

in which formula (I'''a) or (I'''b):
- $R^1$, $R^2$, $R^3$ and $R^4$, which may be identical or different, represent a hydrogen atom or a ($C_1$-$C_6$)alkyl group; preferably $R^2$ and $R^3$ represent a hydrogen atom and $R^1$ and $R^4$, which may be identical or different, represent a hydrogen atom or a ($C_1$-$C_4$)alkyl group;
- $R^5$, $R^6$, $R^7$, Re and $R^9$, which may be identical or different, represent i) a hydrogen atom or ii) a halogen atom such as Cl, Br or F, iii) a group OR in which R represents a hydrogen atom or $Q^+$ as described previously, or a ($C_1$-$C_3$)alkyl group, a group from among iv) aryl such as benzene, v) aryl($C_1$-$C_3$)alkyl such as benzyl, vi) cyano, vii) nitro, viii) ($C_1$-$C_3$)alkylthio, ix) amino $NR^{10}R^{11}$ with $R^{10}$ and $R^{11}$, which may be identical or different, representing a) a hydrogen atom or b) a ($C_1$-$C_8$)alkyl group optionally substituted with one or more groups chosen from:
  - cyano,
  - ($C_1$-$C_3$)alkoxy,
  - hydroxyl, and
  - ($C_1$-$C_3$)alkylcarbonyl;
- in particular $R^{10}$ and $R^{11}$, which may be identical or different, represent a hydrogen atom or a ($C_1$-$C_6$)alkyl group substituted with one or more hydroxyl, cyano or ($C_1$-$C_3$)alkylcarbonyl groups such as methyl, ethyl, butyl, isobutyl, cyanoethyl, methylcarbonylethyl, or hydroxyethyl;
- m represents an integer between 1 and 18 inclusive, particularly an integer between 2 and 16 inclusive; preferentially an integer between 3 and 10; more preferentially an integer between 4 and 6;
- M' represents an anionic counterion derived from salts of organic or mineral acids preferably originating from Y;

it being understood that when the molecule comprises an alkoxide group, then M' and $Q^+$ may be absent to ensure the electrical neutrality of said molecule.

According to one embodiment of the invention, the dye(s) are of formula (I'''a) with:

| $R^1$ | $R^2$ | $R^3$ | $R^4$ | $R^5$ | $R^6$ | $R^7$ | $R^8$ | $R^9$ | m |
|---|---|---|---|---|---|---|---|---|---|
| H | H | H | H | H | H | $OCH_3$ | $OCH_3$ | $OCH_3$ | 2 |
| H | H | H | H | OH | $OCH_3$ | H | H | H | 2 |
| H | H | H | H | H | H | H | H | H | 2 |
| H | H | H | H | H | $OCH_3$ | $OCH_3$ | H | H | 2 |
| H | H | H | H | OH | H | OH | H | H | 6 |
| H | H | H | H | $OCH_3$ | H | $OCH_3$ | $OCH_3$ | H | 6 |
| H | H | H | H | H | H | OH | H | H | 6 |
| H | H | H | H | $OCH_3$ | H | H | H | F | 2 |
| H | H | H | H | H | H | C(O)—OH | H | H | 2 |
| H | H | H | H | H | H | Isopropyl | H | H | 2 |
| H | H | H | H | H | H | $N(CH_2CH_2C(O)CH_3)_2$ | H | H | 2 |
| H | H | H | H | OH | H | $OCH_3$ | H | H | 2 |
| H | H | H | H | H | H | OH | H | H | 2 |
| H | H | H | H | H | $OCH_3$ | OH | OH | H | 2 |
| H | H | H | H | H | $CH_3$ | $OCH_2Ph$ | $CH_3$ | H | 2 |
| H | H | H | H | H | $OCH_3$ | $OCH_3$ | $OCH_3$ | H | 2 |
| H | H | H | H | H | $OCH_3$ | $OCH_3$ | $OCH_3$ | H | 6 |
| H | H | H | H | H | H | $N(CH_3)_2$ | H | H | 6 |
| H | H | H | H | H | H | $OCH_3$ | $OCH_3$ | $OCH_3$ | 6 |
| H | H | H | H | H | H | Phenyl | H | H | 6 |
| H | H | H | H | H | $OCH_3$ | $OCH_3$ | H | H | 6 |
| H | H | H | H | H | H | C(O)—OH | H | H | 6 |
| H | H | H | H | H | H | N(n-Butyl)$_2$ | H | H | 2 |
| H | H | H | H | H | H | $OCH_3$ | $OCH_3$ | H | 3 |
| H | H | H | H | H | H | $OCH_3$ | $OCH_3$ | H | 2 |
| H | H | H | H | H | H | $OCH_3$ | $OCH_3$ | H | 5 |
| H | H | H | H | H | H | $OCH_3$ | H | H | 3 |
| H | H | H | H | H | H | $N(CH_3)_2$ | H | H | 3 |
| H | H | H | H | H | H | H | H | H | 3 | and also the organic or mineral acid or base salts thereof, the optical isomers, geometrical isomers and tautomers thereof, and the solvates thereof such as hydrates.

According to one embodiment, the dye(s) are of formula (I'''b) with:

| $R^1$ | $R^2$ | $R^3$ | $R^4$ | $R^5$ | $R^6$ | $R^7$ | $R^8$ | $R^9$ | m |
|---|---|---|---|---|---|---|---|---|---|
| $CH_3$ | H | H | H | OH | H | $OCH_3$ | H | H | 2 |
| $CH_3$ | H | H | H | H | H | $OCH_3$ | $OCH_2$—Ph | H | 2 |
| $CH_3$ | H | H | H | H | H | H | H | $OCH_3$ | 2 |
| $CH_3$ | H | H | H | F | H | H | H | H | 2 |
| $CH_3$ | H | H | H | H | H | H | OPh | H | 2 |
| $CH_3$ | H | H | H | H | H | $N(CH_2CH_2OAc)_2$ | H | H | 2 |
| $CH_3$ | H | H | H | $OCH_3$ | H | $OCH_3$ | $OCH_3$ | H | 2 |
| $CH_3$ | H | H | H | H | H | H | $CH_3$ | H | 2 |
| $CH_3$ | H | H | H | H | H | OH | H | H | 2 |
| $CH_3$ | H | H | H | H | $OCH_3$ | $OCH_3$ | $OCH_3$ | H | 2 |

-continued

| R¹ | R² | R³ | R⁴ | R⁵ | R⁶ | R⁷ | R⁸ | R⁹ | m |
|---|---|---|---|---|---|---|---|---|---|
| CH₃ | H | H | H | H | OCH₃ | OH | OH | H | 2 |
| CH₃ | H | H | H | H | H | OCH₃ | OCH₃ | OCH₃ | 2 |
| CH₃ | H | H | H | H | H | H | OCH₃ | OH | 2 |
| CH₃ | H | H | H | H | H | N(n-butyl)₂ | H | H | 2 |
| CH₃ | H | H | H | H | OCH₃ | OCH₃ | H | H | 2 |
| CH₃ | H | H | H | H | H | H | H | H | 2 |
| CH₃ | H | H | H | H | H | i-propyl | H | H | 2 |
| H | H | H | H | H | H | OH | H | H | 6 |
| H | H | H | H | H | OCH₃ | OCH₃ | OCH₃ | H | 6 |
| H | H | H | H | OH | H | OCH₃ | H | H | 2 |
| H | H | H | H | OCH₃ | H | H | OCH₃ | OCH₃ | 2 |
| H | H | H | H | H | H | H | H | Br | 2 |
| H | H | H | H | H | H | OH | H | H | 2 |
| H | H | H | H | H | H | N(CH₃)₂ | H | H | 6 |
| H | H | H | H | OCH₃ | OCH₃ | OCH₃ | H | H | 6 |
| H | H | H | H | OH | OCH₃ | H | H | H | 6 |
| H | H | H | H | H | OCH₃ | OCH₃ | H | H | 6 |
| H | H | H | H | H | OCH₃ | OCH₃ | H | H | 2 |
| H | H | H | H | H | H | C(O)—OH | H | H | 6 |
| H | H | H | H | H | H | C(O)—OH | H | H | 2 |
| H | H | H | H | H | H | i-propyl | H | H | 2 |
| H | H | H | H | H | H | N(CH₃)CH₂CH₂CN | H | H | 2 |
| H | H | H | H | H | H | OCH₃ | OCH₂Ph | H | 2 |
| H | H | H | H | H | H | H | OPh | H | 2 |
| H | H | H | H | H | H | N(CH₂CH₂C(O)CH₃)₂ | H | H | 2 |
| H | H | H | H | OH | H | OCH₃ | H | H | 6 |
| H | H | H | H | H | OCH₃ | OCH₃ | OCH₃ | H | 2 |
| H | H | H | H | OCH₃ | H | OCH₃ | OCH₃ | H | 6 |
| H | H | H | H | H | H | H | CH₃ | H | 2 |
| H | H | H | H | H | H | N(CH₃)CH₂CH₂OH | H | H | 2 |
| CH₃ | H | H | H | H | H | N(CH₃)₂ | H | H | 2 | and also the organic or mineral acid or base salts thereof, the geometrical isomers and tautomers thereof, and the solvates thereof such as hydrates.

Another subject of the invention is novel dyes chosen from those of formulae (I″″a) and (I″″b) below:

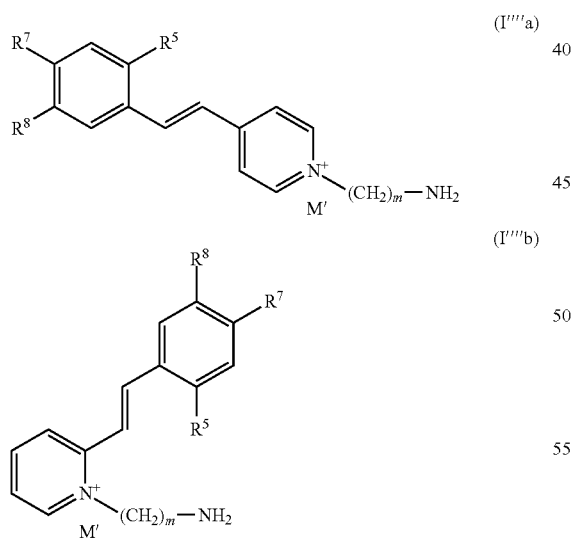

in which formulae (I″″a) and (I″″b) $R^5$, $R^7$, $R^8$ and m are as defined previously for (I‴a) and (I‴b), in particular:

$R^5$ and $R^8$, which may be identical or different, represent a hydrogen atom or a $(C_1\text{-}C_4)$alkoxy group such as methoxy;

$R^7$ represents a $(C_1\text{-}C_4)$alkoxy or $NR^{10}R^{11}$ group with $R^{10}$ and $R^{11}$, which may be identical or different, representing a) a hydrogen atom, or b) a $(C_1\text{-}C_8)$alkyl group optionally substituted with one or more groups chosen from i) cyano, ii) $(C_1\text{-}C_3)$alkoxy, iii) hydroxyl, and iv) $(C_1\text{-}C_3)$alkylcarbonyl;

in particular, $R^{10}$ and $R^{11}$, which may be identical or different, represent a hydrogen atom, or a $(C_1\text{-}C_6)$alkyl group optionally substituted with one or more hydroxyl, cyano or $(C_1\text{-}C_3)$alkylcarbonyl groups such as methyl, ethyl, butyl, isobutyl, cyanoethyl, methylcarbonylethyl, or hydroxyethyl; preferably, $R^{10}$ and $R^{11}$, which may be identical or different, represent a $(C_1\text{-}C_6)$alkyl group optionally substituted with one or more hydroxyl groups such as hydroxyethyl;

m represents an integer between 1 and 18 inclusive; particularly an integer between 2 and 16 inclusive; preferentially an integer between 3 and 10; more preferentially an integer between 4 and 6; and M' represents an anionic counterion, derived from a salt of an organic or mineral acid, or from an organic or mineral base that ensures the electrical neutrality of the molecule.

According to one embodiment, the novel dye(s) are of formula (I″″a) or (I″″b) with:

| R⁵ | R⁷ | R⁸ | m |
|---|---|---|---|
| H | N(CH₂CH₂OH)₂ | H | 2 |
| H | N(CH₂CH₂OH)₂ | H | 3 |
| H | N(CH₂CH₂OH)₂ | H | 4 |
| H | N(CH₂CH₂OH)₂ | H | 5 |
| H | N(CH₂CH₂OH)₂ | H | 6 |
| H | N(CH₂CH₂OH)₂ | H | 8 |
| H | N(CH₂CH₂OH)₂ | H | 10 |
| H | N(CH₂CH₂OH)₂ | H | 12 |

-continued

| $R^5$ | $R^7$ | $R^8$ | m |
|---|---|---|---|
| H | $N(CH_2CH_2OH)_2$ | H | 14 |
| H | $N(CH_2CH_2OH)_2$ | H | 16 | and

| $R^5$ | $R^7$ | $R^8$ | m |
|---|---|---|---|
| $OCH_3$ | $OCH_3$ | $OCH_3$ | 2 |
| $OCH_3$ | $OCH_3$ | $OCH_3$ | 3 |
| $OCH_3$ | $OCH_3$ | $OCH_3$ | 3 |
| $OCH_3$ | $OCH_3$ | $OCH_3$ | 4 |
| $OCH_3$ | $OCH_3$ | $OCH_3$ | 5 |
| $OCH_3$ | $OCH_3$ | $OCH_3$ | 8 |
| $OCH_3$ | $OCH_3$ | $OCH_3$ | 10 |
| $OCH_3$ | $OCH_3$ | $OCH_3$ | 12 |
| $OCH_3$ | $OCH_3$ | $OCH_3$ | 14 |
| $OCH_3$ | $OCH_3$ | $OCH_3$ | 16 | and also the organic or mineral acid or base salts thereof, the geometrical isomers and tautomers thereof, and the solvates thereof such as hydrates.

According to another particular embodiment of the invention, the direct dye(s) are chosen from those of formulae (IIa) and (IIb), preferably (IIa) and in particular (II'a) having the following formula:

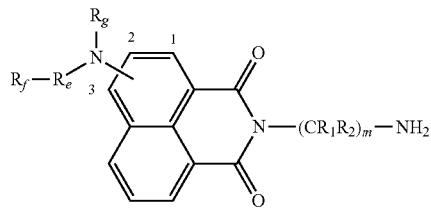

(II'a)

and also the organic or mineral acid or base salts thereof, the optical isomers, geometrical isomers and tautomers thereof, and the solvates thereof such as hydrates;
in which formula (II'a) $R_1$, $R_2$, $R_e$, $R_f$, $R_g$ and m are as defined previously; preferably, the amino group $R_f$—$R_e$—$N(R_g)$— is on the carbon atom in position 3;
according to a particular embodiment of the invention, $R_1$ and $R_2$, which may be identical or different, represent a hydrogen atom or a $(C_1$-$C_6)$alkyl group, preferentially a hydrogen atom; $R_g$ represents a $(C_1$-$C_4)$alkyl group, preferably a hydrogen atom; $R_e$ represents an unsubstituted $(C_1$-$C_6)$alkylene group, $R_f$ represents a (di)$(C_1$-$C_4)$(alkyl)amino group; m represents an integer between 1 and 16 inclusive, preferentially an integer between 2 and 14 inclusive; more preferentially an integer between 3 and 12; more particularly an integer between 4 and 10.

Preferably, the dye(s) of the invention are chosen from those having the following formula:

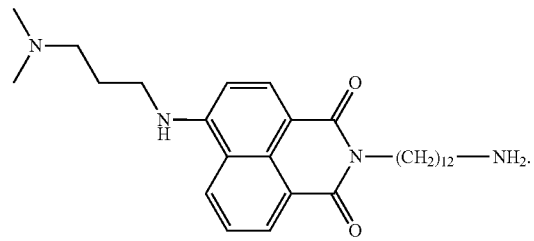

Process for Synthesizing the Direct Dyes of the Invention:

The dyes of the invention are synthesized from commercial reagents or may be synthesized via methods known to those skilled in the art. Mention may be made especially of Angewandte Chemie [Applied Chemistry], International Edition (2004), 43(46), 6331-6335.

According to a particular embodiment of the invention, the dyes are chosen from the azo dyes of formula (IA) below:

(IA)

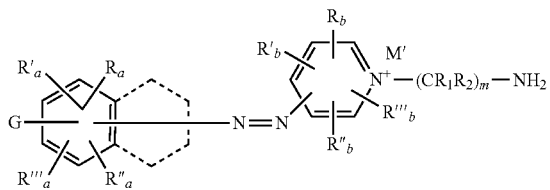

and also the organic or mineral acid or base salts thereof, the optical isomers, geometrical isomers and tautomers thereof, and the solvates thereof such as hydrates, in which formula (IA) G, $R_a$, $R'_a$, $R''_a$, $R_b$, $R'_b$, $R''_b$, $R_1$, $R_2$, M' and m are as defined previously for (I) preferably according to (1').

The process for synthesizing the compounds of formula (IA) used in the invention consists for example in performing the following steps:

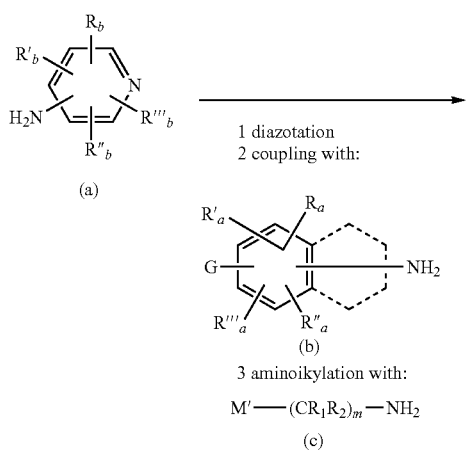

-continued

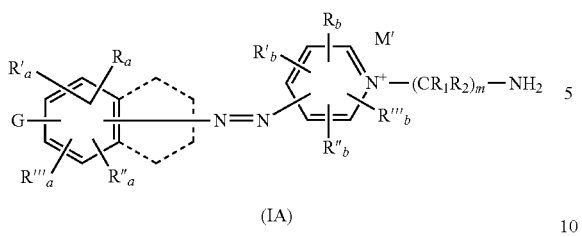

(IA)

with G, $R_a$, $R'_a$, $R''_a$, $R_b$, $R'_b$, $R''_b$, $R_1$, $R_2$, M' and m as defined previously.

According to this process, a first step of diazotization of an amino pyridine (a) is performed in a manner known to those skilled in the art. They may be obtained from the references described in Color Chemistry, H. Zollinger, $3^{rd}$ Edn, Wiley VCH, pages 166-169.

Thus, said amine is placed in contact with phosphoric acid and tert-butyl nitrite. Usually, this reaction is carried out at a temperature between −20° C. and 30° C.; preferably between −10° C. and 20° C., at a pH of between 0 and 12.

Conventionally, the reaction is carried out in the presence of a suitable solvent, among which mention may be made of water, alcohols, in particular aliphatic alcohols comprising up to 4 carbon atoms, organic acids, for example a carboxylic acid or sulfonic acid comprising up to 10 carbon atoms, and/or mineral acids of the type such as hydrochloric or sulfuric acid.

Once the reaction has been performed, the product obtained is coupled with a compound of the aniline type (b) followed by an aminoalkylation with product (c), preferably by heating at the reflux point of the solvent, to give the compound of formula (IA).

Conventionally, this reaction is carried out in the presence of a solvent which may be that of the preceding step.

The temperature is conventionally between −15° C. and 30° C.; preferably between −10° C. and 20° C., at a pH preferably of between 0 and 8.

The product may be isolated via the techniques known to those skilled in the art (precipitation, evaporation, etc.).

According to another particular embodiment of the invention, the dyes of the invention are chosen from the styryl dyes of formula (I') as defined previously.

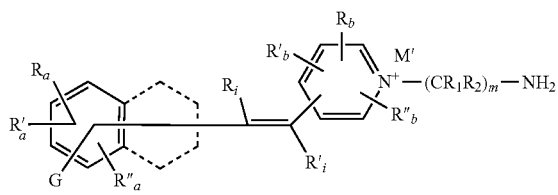

The compounds of formula (I') may be obtained according to the following synthetic route:

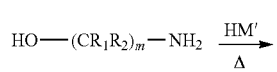

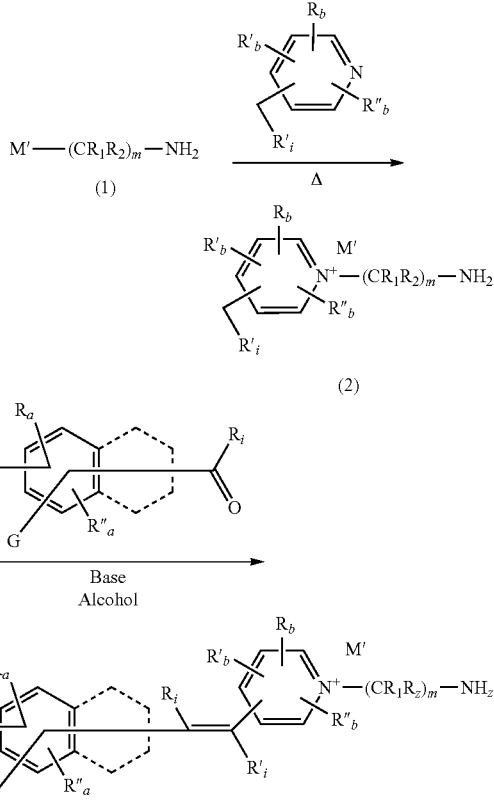

in which G, $R_a$, $R'_a$, $R''_a$, $R_b$, $R'_b$, $R''_b$, $R_i$, $R'_i$, $R_1$, $R_2$ and m are as defined previously for (I').

The first step consists in functionalizing an amino alcohol derivative with a leaving (electrofugal) group such as a halogen, for example chlorine or bromine, a sulfate or a polyhalosulfate such as triflate. As solvent used in the first step, use may be made of polar aprotic solvents such as halogenated solvents chosen in particular from dichloromethane, 1,2-dichloroethane, 1,1,1-trichloroethane, chloroform, acetonitrile, toluene, dioxane, tetrahydrofuran, 1,2-dimethoxyethane, cyclohexane, or a mixture of these solvents.

The reaction is performed at a temperature of between 20° C. and 120° C. and preferably at the boiling point of the solvent.

The derivative (1) may be obtained by evaporation of the reaction solvent, or by precipitation from a solvent in which the expected product is insoluble, for instance acetone, ethyl acetate, isopropyl acetate, ethyl ether or isopropyl ether.

The derivative (1) is then reacted with the pyridine derivative, preferably without solvent, or in the presence of a solvent of polar protic type, in particular an alcohol such as ethanol, isopropanol or n-butanol, at a temperature close to the boiling point of the solvent (in the case of a reaction in the presence of solvent) or at the boiling point of the pyridine derivative reacted in the case of a solvent-free reaction.

The derivative (2) is thus obtained after evaporation of the solvent.

It is then reacted in the presence of the pyridine derivative in a polar protic solvent of alcohol type such as methanol, ethanol, isopropanol or n-butanol in the presence of an organic base in catalytic or stoichiometric amount, for instance pyrrolidine, or in the presence of an organic salt which buffers the medium, for instance pyrrolidine acetate.

The expected product may precipitate from the medium, in which case it is isolated by filtration. In the contrary case, it may be obtained by precipitation or recrystallization from a solvent in which it is insoluble or very sparingly soluble, for instance acetone, ethyl acetate, isopropyl acetate, ethyl ether or isopropyl ether.

The composition according to the invention contains, in a cosmetic medium, an amount of dyes of formula (I), (IIa) or (IIb) as defined previously, generally of between 0.001% and 30% inclusive, relative to the total weight of the composition.

Preferably, the amount of dyes of formula (I), (IIa) or (IIb) is between 0.01% and 5% by weight inclusive relative to the total weight of the composition. By way of example, the dye(s) are in an amount of between 0.01% and 2% inclusive.

Preferably, the composition of the dyeing and/or lightening process of the invention is in liquid form and contains one or more cationic direct dyes of formula (I), (IIa) or (IIb) as defined previously.

The cosmetically acceptable salt of organic or mineral acid and counterion of the dyes of the invention They are chosen from the "organic or mineral acid salt" and "anionic counterion" as defined previously.

Moreover, the addition salts that may be used in the context of the invention may be chosen from salts of addition with a cosmetically acceptable base such as basifying agents as defined below, for instance alkali metal hydroxides such as sodium hydroxide, potassium hydroxide, aqueous ammonia, amines or alkanolamines.

The Alkaline Agent:

According to a particular embodiment of the invention, the composition comprises one or more alkaline agents. This agent may be chosen from mineral or organic or hybrid alkaline agents or mixtures thereof.

The mineral alkaline agent(s) are preferably chosen from aqueous ammonia, alkali metal carbonates or bicarbonates such as sodium or potassium carbonates and sodium or potassium bicarbonates, sodium hydroxide or potassium hydroxide, or mixtures thereof.

According to an advantageous embodiment of the invention, the alkaline agent(s) are organic amines, i.e. they contain at least one substituted or unsubstituted amino group.

The organic alkaline agent(s) are preferably chosen from organic amines with a $pK_b$ at 25° C. of less than 12, preferably of less than 10 and more advantageously still of less than 6. It should be noted that it concerns the $pK_b$ corresponding to the function having the highest basicity.

Hybrid compounds that may be mentioned include the salts of the amines mentioned previously with acids such as carbonic acid or hydrochloric acid.

The organic alkaline agent(s) are chosen, for example, from alkanolamines, oxyethylenated and/or oxypropylenated ethylenediamines, amino acids and the compounds having formula (II) below:

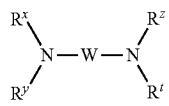
(III)

in which formula (XX):
W is a divalent $C_1$-$C_6$ alkylene radical optionally substituted with a hydroxyl group or a $C_1$-$C_6$ alkyl radical, and/or optionally interrupted with one or more heteroatoms such as oxygen or $NR^u$;
$R^x$, $R^y$, $R^z$ $R^t$ and $R^u$, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising from one to three identical or different $C_1$-$C_4$ hydroxyalkyl radicals are in particular suitable for performing the invention.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

As amino acids that may be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (IV) below, R—$CH_2$—CH(NH)—C(O)—OH, with R representing a group chosen from imidazolyl, in particular 4-imidazolyl, aminopropyl; aminoethyl, —$(CH_2)_2$—NH—C(O)—$NH_2$ and —$(CH_2)_2$—NH—C(=NH)—$NH_2$.

The compounds corresponding to the formula (IV) are in particular histidine, lysine, arginine, ornithine and citrulline.

The organic amine may also be chosen from organic amines of heterocyclic type.

Besides histidine that has already been mentioned in the amino acids, mention may be made in particular of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and balenine.

The organic amine is chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Mention may be made in particular of the use of guanidine carbonate or monoethanolamine hydrochloride as hybrid compounds.

The composition of the invention preferably contains one or more alkanolamines and/or one or more basic amino acids, more advantageously one or more alkanolamines. Even more preferentially, the organic amine is monoethanolamine.

According to a particular embodiment, the composition of the invention comprises as alkaline agent one or more alkanolamines.

Preferably, the alkanolamine is ethanolamine (or monoethanolamine).

In one variant of the invention, the composition comprises, as alkaline agent, one or more alkanolamines (preferably ethanolamine) and aqueous ammonia. In this variant, the alkanolamine(s) are present in a predominant amount relative to the aqueous ammonia.

Advantageously, the composition according to the invention has a content of alkaline agent(s) ranging from 0.01% to 30% by weight, preferably from 0.1% to 20% by weight and better still from 1% to 10% by weight relative to the weight of said composition.

Adjuvants:

The composition of the invention as defined previously may also contain various adjuvants conventionally used in hair dye compositions, such as anionic, cationic or nonionic surfactants or mixtures thereof, anionic, cationic, nonionic, amphoteric or zwitterionic polymers or mixtures thereof, mineral or organic thickeners, penetrants, sequestrants, fragrances, buffers, dispersants, conditioning agents, for instance volatile or non-volatile and modified or unmodified silicones, film-forming agents, ceramides, preserving agents or opacifiers.

The above adjuvants are preferably present in an amount for each of them of between 0.01% and 20% by weight relative to the weight of the composition.

Needless to say, a person skilled in the art will take care to select this or these optional additional compound(s) such that the advantageous properties intrinsically associated with the dye composition in accordance with the invention are not, or are not substantially, adversely affected by the envisaged addition(s).

Additional Dyes:

The composition comprising the dye(s) of formula (I), (IIa) or (IIb) as defined previously of the process of the invention may also contain one or more additional direct dyes other than the disulfide, thiol or protected-thiol direct dyes of formula (I), (IIa) or (IIb) according to the invention. These direct dyes are chosen, for example, from those conventionally used in direct dyeing, and among which mention may be made of any commonly used aromatic and/or non-aromatic dye such as neutral, acidic or cationic nitrobenzene direct dyes, neutral, acidic or cationic azo direct dyes, natural direct dyes, neutral, acidic or cationic quinone and in particular anthraquinone direct dyes, azine, triarylmethane, indoamine, methine, styryl, porphyrin, metalloporphyrin, phthalocyanine and cyanine methine direct dyes, and fluorescent dyes other than the dyes of formula (I), (IIa) or (IIb).

Among the natural direct dyes, mention may be made of lawsone, juglone, alizarin, purpurin, carminic acid, kermesic acid, purpurogallin, protocatechaldehyde, indigo, isatin, curcumin, spinulosin, apigenidin and oreceins. Use may also be made of extracts or decoctions comprising these natural dyes and in particular henna-based poultices or extracts.

According to the invention, the additional direct dye(s) used according to the invention preferably represent from 0.001% to 10% by weight approximately relative to the total weight of the dye composition comprising the dye(s) of formula (I), (IIa) or (IIb) as defined previously and even more preferentially from 0.05% to 5% by weight approximately.

The composition comprising the dye(s) of formula (I), (IIa) or (IIb) as defined above of the process of the invention may also contain one or more oxidation bases and/or one or more couplers conventionally used for the dyeing of keratin fibres.

Among the oxidation bases, mention may be made of para-phenylenediamines, bis(phenyl)alkylenediamines, para-aminophenols, bis-para-aminophenols, ortho-aminophenols and heterocyclic bases, and the addition salts thereof.

Among these couplers, mention may be made especially of meta-phenylenediamines, meta-aminophenols, meta-diphenols, naphthalene-based couplers and heterocyclic couplers, and the addition salts thereof.

The coupler(s) are each generally present in an amount of between 0.001% and 10% by weight and preferably between 0.005% and 6% by weight relative to the total weight of the dye composition.

The oxidation base(s) present in the dye composition are each generally present in an amount of between 0.001% and 10% by weight and preferably between 0.005% and 6% by weight relative to the total weight of the dye composition.

In general, the addition salts of the oxidation bases and couplers that may be used in the context of the invention are chosen especially from salts of addition with an acid, such as hydrochlorides, hydrobromides, sulfates, citrates, succinates, tartrates, lactates, tosylates, benzenesulfonates, phosphates and acetates, and salts of addition with a base, such as alkali metal hydroxides, for instance sodium hydroxide, potassium hydroxide, aqueous ammonia, amines or alkanolamines.

According to one particular embodiment, the composition of the process of the invention contains at least one oxidation base and optionally at least one coupler as defined above.

The process of the invention may also use another composition that comprises one or more chemical oxidizing agents. The term "chemical oxidizing agent" means chemical oxidizing agents other than atmospheric oxygen, such as those described previously.

The use of hydrogen peroxide is particularly preferred.

The content of oxidizing agent(s) is generally between 1% and 40% inclusive by weight relative to the weight of the composition and preferably between 1% and 20% by weight relative to the weight of the composition containing them.

According to a preferred embodiment of the invention, the composition of the process of the invention does not contain any chemical oxidizing agent. In particular, the process of the invention does not use any chemical oxidizing agent. Preferably, neither the composition nor the process contain or use any oxidation base and/or coupler.

The pH:

The pH of the composition according to the invention is particularly between 2 and 12 approximately and preferably between 3 and 11 approximately. It may be adjusted to the desired value by means of acidifying or basifying agents usually used in the dyeing of keratin fibres, or alternatively using standard buffer systems.

The pH of the composition is preferentially inclusively between 6 and 9, particularly between 7 and 9, and more particularly between 7.5 and 9.

Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

Among the alkaline agents that may be mentioned, for example, are aqueous ammonia, alkali metal carbonates, alkanolamines such as monoethanolamines, diethanolamines and triethanolamines, and other alkaline agents as defined previously.

Forms of the Composition:

The dye composition comprising the dye(s) of formula (I), (IIa) or (IIb) as defined above may be in various galenical forms, such as in the form of liquids, lotions, creams or gels or in any other form suitable for dyeing keratin fibres. It may also be packaged under pressure in an aerosol container in the presence of a propellant or in a non-aerosol container and may form a foam.

Dyeing Processes of the Invention

One subject of the invention is a process for dyeing and/or lightening keratin materials, in particular keratin fibres, preferably human keratin fibres such as the hair, which consists in applying to said materials a cosmetic composition comprising at least one direct dye chosen from those of formulae (I), (IIa) and (IIb) as defined previously.

According to a particular embodiment, the dyeing process is used for dyeing light keratin materials, more particularly light keratin fibres preferably with a tone depth of greater than 6 (TD>6), which consists in applying to said materials a cosmetic composition comprising at least one direct dye chosen from those of formulae (I), (IIa) and (IIb) as defined previously.

According to another particular embodiment of the invention, the dyeing and lightening process is performed on dark keratin material, more particularly dark keratin fibres preferably with a tone depth TD of less than or equal to 6, more preferentially less than or equal to 4, such as 2, which consists in applying to said materials a cosmetic composition comprising at least one direct dye chosen from those of formulae (I), (IIa) and (IIb) as defined previously.

According to a particular embodiment, when it is desired to lighten dark keratin materials, a cosmetic composition comprising at least one fluorescent direct dye chosen from those of formulae (I'), (I''), (I'''a), (I'''b), (I''''a), (I''''b), (IIa) and (IIb) as defined previously is applied to said materials.

The leave-in time of the dye composition, i.e. the composition comprising the dye(s) of formula (I), (IIa) or (IIb) as defined previously, is between 5 minutes and 1 hour inclusive and preferably between 10 minutes and 40 minutes.

According to one embodiment of the invention, the dyeing process is a process for dyeing light keratin materials, in particular light keratin fibres with a tone depth of greater than 6, comprising i) a step of applying to said keratin materials cosmetic composition which comprises one or more direct dyes of formula (I), (IIa) or (IIb) as defined previously and ii) a step of applying a cosmetic composition which comprises one or more blue dyes, in particular direct blue dyes, preferably cationic blue dyes; steps i) and ii) possibly being performed together or separately. According to a particular embodiment of the invention, step i) is performed before step ii). According to another particular embodiment of the invention, steps i) and ii) are performed simultaneously. One variant of the latter embodiment is to apply to the light keratin materials a cosmetic composition which comprises one or more direct dyes of formula (I), (IIa) or (IIb) as defined previously and one or more blue dyes, in particular direct blue dyes, preferably cationic blue dyes.

Preferably, the process for dyeing light keratin materials using one or more direct dyes of formula (I), (IIa) or (IIb) as defined previously and one or more blue dyes, in particular direct blue dyes, preferably cationic blue dyes, does not use any other dyes.

This process for dyeing light keratin materials using a combination of one or more direct dyes of formula (I), (IIa) or (IIb) as defined previously and of blue dyes makes it possible to obtain dark brown, dark chestnut-brown or even black colours.

The dye composition(s) are generally applied at room temperature. However, they may be applied at temperatures ranging from 20 to 180° C.

The dyeing and/or lightening process according to the invention may be followed by shampooing with a standard shampoo and/or drying of the keratin fibres.

According to a particular embodiment, neither the composition nor the process of the invention involves a reducing agent.

According to a particular embodiment, neither the composition nor the process of the invention involves a chemical oxidizing agent.

The examples that follow serve to illustrate the invention without, however, being limiting in nature.

EXAMPLES a) Preparation Examples

Example 1: Preparation of 1-(6-aminohexyl)-4-[2-{4-[bis(2-hydroxyethyl)amino]phenyl}ethenyl]pyridinium Chloride Hydrochloride

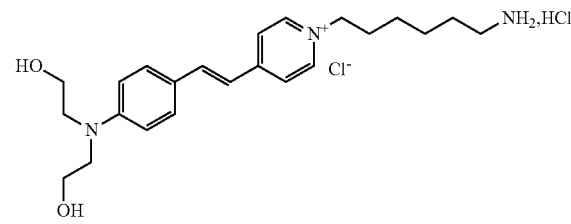

1st Step

Synthesis of 6chlorohexan-1-amine Hydrochloride

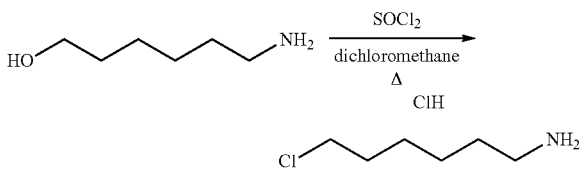

Procedure:

20 g of 6-amino-1-hexanol (0.171 mol) were placed 50 ml of dichloromethane in a 250 ml three-necked round-bottomed flask equipped with a condenser, an argon inlet, a thermometer, a bubbler and a magnetic stirrer.

15 ml of thionyl chloride (0.205 mol) were then added dropwise. The reaction medium was then refluxed. The reaction progress was monitored by TLC in an elution system: 9/1 dichloromethane/methanol, with UV revelation.

The reaction medium was then evaporated under reduced pressure and dried under vacuum in the presence of $P_2O_5$ to constant weight.

The final product was obtained in the form of a brown paste (quantitative yield).

NMR spectrum and mass spectrum compliant.

2nd Step

Synthesis of 1-(6-aminohexyl)-4-methylpyridinium Chloride Hydrochloride

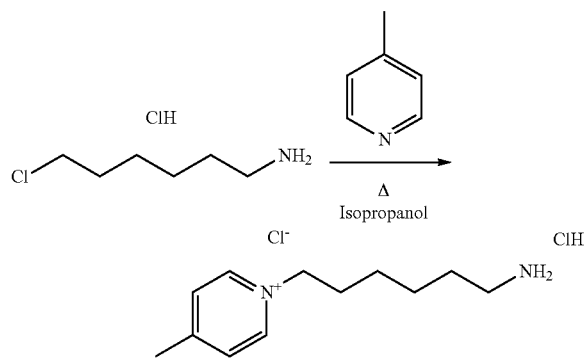

Procedure:

31.12 g of the compound prepared in the preceding step (0.181 mol) and 19.5 ml of 4-picoline (0.199 mol) were placed in 50 ml of isopropanol in a 500 ml round-bottomed flask equipped with a condenser, a magnetic stirrer and a thermometer. The reaction medium was refluxed and the reaction progress was monitored by TLC in an 84/15/1 dichloromethane/methanol/aqueous ammonia elution system followed by revelation with potassium permanganate solution.

The reaction medium was cooled to 50° C. and 300 ml of acetone were then added. The reaction medium was stirred for 30 minutes at room temperature. The precipitate was filtered off through a polypropylene gauze, washed thoroughly with acetone and dried under vacuum in the presence of $P_2O_5$ to constant weight.

The final product was obtained in the form of a dark brown powder.

NMR spectrum compliant.

3rd Step

Synthesis of 1-(6-aminohexyl)-4-[2-{4-[bis(2-hydroxyethyl)amino]phenyl}ethenyl]pyridinium Chloride Hydrochloride

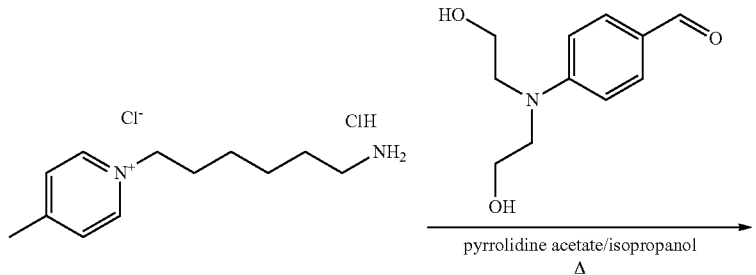

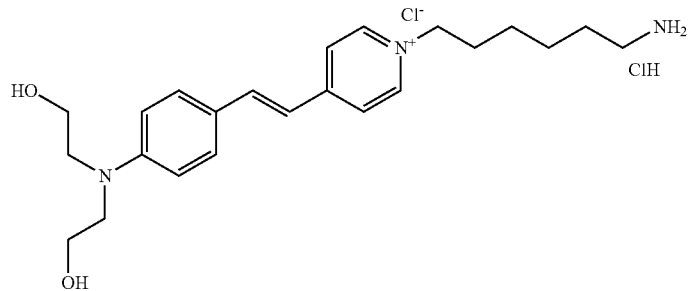

Procedure:

Preparation of a Pyrrolidine Acetate Solution:

2.8 ml of pyrrolidine (0.033 mol) were placed in 10 ml of isopropanol in a 50 ml conical flask. This solution was cooled to between 0 and 5° C. using an ice bath, followed by dropwise addition of 1.9 ml of acetic acid (0.034 mol).

8.8 g of 1-(6-aminohexyl)-4-methylpyridinium chloride hydrochloride (0.033 mol) were placed in 50 ml of isopropanol in a 250 ml round-bottomed flask equipped with a condenser, a magnetic stirrer and a thermometer. 7.6 g of 4-[bis(2-hydroxyethyl)amino]benzaldehyde (0.036 mol) were added and the reaction medium was then stirred at 30° C.

The pyrrolidine acetate solution prepared beforehand was then added to the reaction medium. The reaction medium was brought, with stirring, to 50° C. while monitoring the progress by TLC in an elution system: 84/15/1 dichloromethane/methanol/aqueous ammonia with UV revelation.

The reaction medium was cooled to 40° C. and 150 ml of ethanol were then added. The solution thus obtained was added dropwise into 1.2 litres of acetone with stirring. The precipitate thus formed was filtered off through a polypropylene gauze in a filtration system under forced pressure of argon. The precipitate was washed thoroughly with acetone and dried under vacuum in the presence of $P_2O_5$ to constant weight.

The final product was obtained in the form of a red powder.

NMR spectrum and mass spectrum compliant.

Example 2

Preparation of 1-(2-aminoethyl)-4-[2-{4-[bis(2-hydroxyethyl)amino]phenyl}ethenyl]pyridinium Chloride Hydrochloride

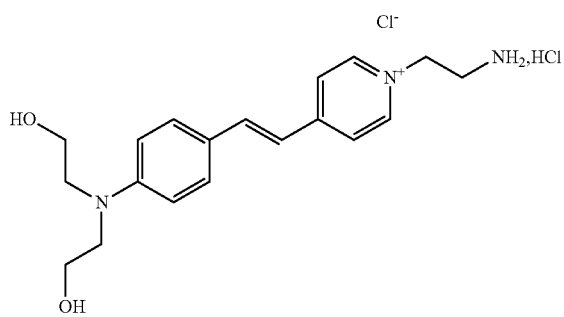

The compound is prepared according to the same procedure as in Example 1, using:
  7.3 g of 1-(2-aminoethyl)-4-methylpyridinium chloride hydrochloride (0.035 mol)
  8 g of 4-[bis(2-hydroxyethyl)amino]benzaldehyde (0.038 mol).

1-(2-Aminoethyl)-4-[2-{4-[bis(2-hydroxyethyl)amino] phenyl}ethenyl]pyridinium chloride hydrochloride is obtained in the form of a red powder.

NMR spectrum and mass spectrum compliant.

Example 3

Preparation of 1-(3-aminopropyl)-4-[2-{4-[bis(2-hydroxyethyl)amino]phenyl}ethenyl]pyridinium Chloride Hydrochloride

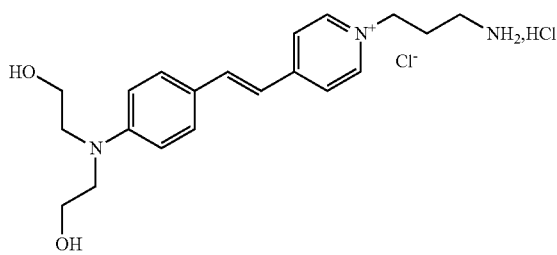

The compound is prepared according to the same procedure as in Example 1, using:
  10 g of 1-(3-aminopropyl)-4-methylpyridinium chloride hydrochloride (0.045 mol)
  10.3 g of 4-[bis(2-hydroxyethyl)amino]benzaldehyde (0.049 mol).

1-(3-Aminopropyl)-4-[(E)-2-{4-[bis(2-hydroxyethyl) amino]phenyl}ethenyl]pyridinium chloride hydrochloride is obtained in the form of a red powder.

NMR spectrum and mass spectrum compliant.

Example 4

Preparation of 1-(5-aminopentyl)-4-[2-{4-[bis(2-hydroxyethyl)amino]phenyl}ethenyl]pyridinium Chloride Hydrochloride

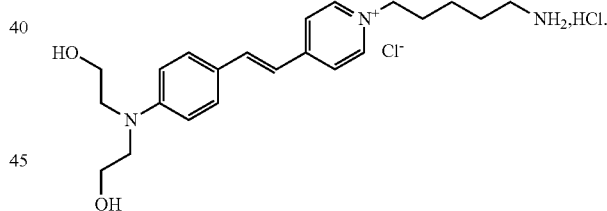

The compound is prepared according to the same procedure as in Example 1, using:
  10 g of 1-(5-aminopentyl)-4-methylpyridinium chloride hydrochloride (0.040 mol)
  9.2 g of 4-[bis(2-hydroxyethyl)amino]benzaldehyde (0.044 mol).

1-(5-Aminopentyl)-4-[2-{4-[bis(2-hydroxyethyl)amino] phenyl}ethenyl]pyridinium chloride hydrochloride is obtained in the form of a red powder.

NMR spectrum and mass spectrum compliant.

b) Dyeing and Lightening Application Examples

Dyeing and Lightening Application Examples b-A) Materials

All the compounds were evaluated i) in direct dyeing on locks (N90W) of natural 90% white hair and ii) in lightening on dark chestnut-brown Japanese hair with a tone depth of 2 (TD2) followed by a shampoo persistence study (10 and 20 shampoo washes).

The colorimetric measurements were taken using a Konica Minolta brand CM-2600d/2500d spectrophotometer. This machine has a wavelength range from 360 nm to 740 nm and can measure in various colorimetric spaces (L*a*b*, L*C*h*, CMC, XYZ . . . ). The data processing software used is the Color Data Software CM-S100W.

In this L* a* b* system, the three parameters denote, respectively, the colour intensity (L*), the green/red colour axis (a*) and the blue/yellow colour axis (b*).

The colour build-up is represented by the colour difference ΔE between the untreated lock and the treated lock: the greater the value of ΔE, the greater the colour build-up. This value is calculated from the following equation (i):

$$\Delta E = \sqrt{(L^*-L_o^*)^2+(a^*-a_o^*)^2+(b^*-b_o^*)^2} \quad (i)$$

In the equation (i), L*, a* and b* represent the values measured on treated locks of hair and $L_o^*$, $a_o^*$ and $b_o^*$ represent the values measured on untreated locks of hair.

The colour chromaticity is calculated according to equation (ii) below:

$$C^* = \sqrt{(a^*)^2+(b^*)^2}$$

in which a* and b* represent the values measured on locks of treated hair. The greater the value of ΔE, the greater the colour chromaticity.

b-B) Protocol

All the compounds synthesized were evaluated at a value of 0.5% by mass in water, i.e.:
Example 1: 1-(6-aminohexyl)-4-[2-{4-[bis(2-hydroxyethyl)amino]phenyl}ethenyl]pyridinium chloride hydrochloride (0.001095 mol)
Example 2: 1-(2-aminoethyl)-4-[2-{4-[bis(2-hydroxyethyl)amino]phenyl}ethenyl]pyridinium chloride hydrochloride (0.001249 mol)
Example 3: 1-(3-aminopropyl)-4-[2-{4-[bis(2-hydroxyethyl)amino]phenyl}ethenyl]pyridinium chloride hydrochloride (0.001207 mol)
Example 4: 1-(5-aminopentyl)-4-[2-{4-[bis(2-hydroxyethyl)amino]phenyl}ethenyl]pyridinium chloride hydrochloride (0.00113 mol)

Application of Cleansing Shampoo (so as to Obtain Clean Hair):

1. Weigh out 0.4 ml of cleansing shampoo per gram of hair in a watch glass.
2. Wet the lock with tap water, passing the lock between the fingers for 5 seconds.
3. Drain the lock of hair dry between two fingers.
4. Apply the cleansing shampoo along the lock of hair (from the root to the end homogeneously).
5. Massage the lock gently between two fingers along its length (so as to work the shampoo into a lather) for 15 seconds from top to bottom (without making knots).
6. Rinse under tap water for 10 seconds, passing the lock between the fingers.
7. Drain the lock dry between two fingers.
8. Comb the lock.
9. Dry the lock with a hairdryer.

The comparative product is a disulfide fluorescent dye having the following structure:

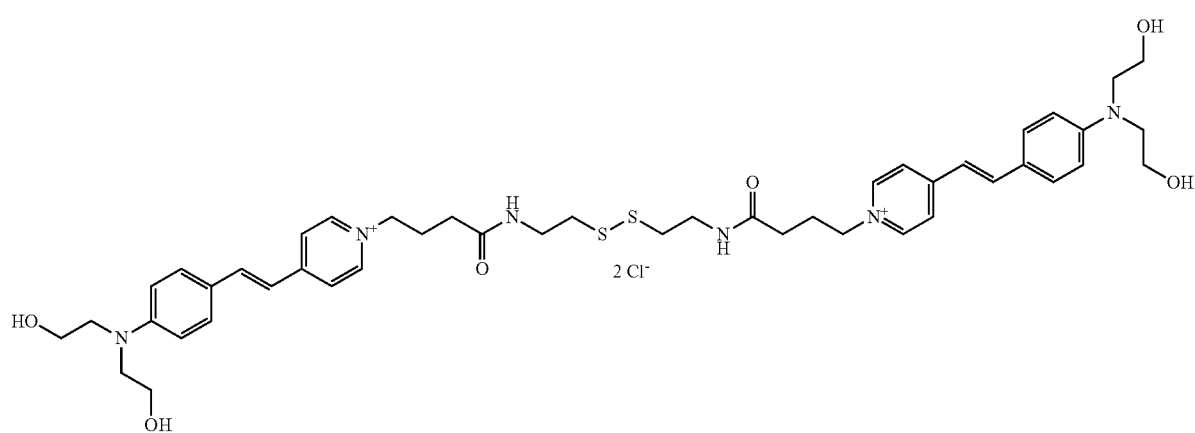

1. Prepare the dye solution at 0.5% w/w in water (10 ml of solution).
2. Place a 1 g lock in a channel.
3. Apply the solution of the test product along the lock of hair (from the root to the end homogeneously; Bath ratio: 1 g of lock of hair per 10 g of composition, BR=10).
4. Leave the composition to stand on the lock for 20 minutes on a hotplate at 25° C.
5. Rinse under tap water for 10 seconds, passing the lock between the fingers.
6. Drain the lock dry between two fingers.
7. Comb the lock.
8. Dry the lock under a hood.

Application of Shampoo (Persistence):
1. Weigh out 0.4 ml of DOP camomile shampoo per gram of hair in a watch glass.
2. Wet the lock with tap water, passing the lock between the fingers for 5 seconds.

3. Drain the lock of hair dry between two fingers.
4. Apply the cleansing shampoo along the lock of hair (from the root to the end homogeneously).
5. Massage the lock gently between two fingers along its length (so as to work the shampoo into a lather) for 15 seconds from top to bottom (without making knots).
6. Rinse under tap water for 10 seconds, passing the lock between the fingers.
7. Drain the lock dry between two fingers.
8. Comb the lock.
9. Repeat steps 4 to 8 as many times as there are shampoo washes to be performed (5, 10 and 20 shampoo washes).
10. Dry the lock under a hood.

b-C) Measurement of the Colour on 90% White (NW) Caucasian Hair

The measurements clearly show the production of a strong, luminous red colouring that is shampoo-fast.

TABLE 1

| Product | No. of shampoo washes | L* (D65) | a* (D65) | b* (D65) | ΔE* (D65) |
|---|---|---|---|---|---|
| Comparative* | | | | | |
| Compound 5 | 0 | 32.52 | 39.53 | 26.50 | 44.21 |
| Compound 5 | 10 | 35.85 | 40.87 | 29.76 | 45.46 |
| Invention** | | | | | |
| Compound 1 | 0 | 36.37 | 44.19 | 37.12 | 51.52 |
| Compound 1 | 10 | 38.42 | 46.87 | 38.15 | 53.79 |
| Compound 1 | 20 | 40.11 | 45.93 | 41.37 | 54.41 |
| Compound 2 | 0 | 27.23 | 34.54 | 22.53 | 41.29 |
| Compound 2 | 10 | 34.22 | 45.49 | 31.89 | 50.80 |
| Compound 2 | 20 | 36.60 | 49.11 | 36.48 | 55.27 |
| Compound 3 | 0 | 33.26 | 44.15 | 32.21 | 50.10 |
| Compound 3 | 10 | 38.15 | 47.52 | 36.26 | 53.47 |
| Compound 3 | 20 | 37.96 | 46.30 | 37.86 | 53.26 |
| Compound 4 | 0 | 35.03 | 39.67 | 32.29 | 45.83 |
| Compound 4 | 10 | 39.68 | 46.57 | 39.29 | 53.88 |
| Compound 4 | 20 | 41.97 | 46.95 | 42.83 | 55.77 |

* at pH 9.5 and after a reductive pretreatment, results obtained on natural grey hair containing 90% white hairs (N90W).
** at spontaneous pH without reductive pretreatment, results obtained on natural grey hair containing 90% white hairs (N90W).

It is seen that the build-up is significantly better for the compounds according to the invention than for the comparative dye 5, even after several shampoo washes. It is seen that the colour build-ups are very good with the compounds according to the invention.

Comparative

TABLE 2

| Test compounds | L* (D65) | a* (D65) | b* (D65) | ΔE* (D65) | C* (D65) |
|---|---|---|---|---|---|
| Example 1 (invention) | 27.23 | 34.54 | 22.53 | 41.28 | 41.23 |
| Example 6 (comparative) | 48.21 | 21.84 | 19.85 | 21.91 | 29.51 |

It is seen that the process of the invention makes it possible to significantly improve the intensity, the colour build-up and the chromaticity relative to comparative compound 6.

b-D) Measurement of the Lightening on TD2 Japanese Hair

The results of the reflectance curves are given in plates 1 and 2.

It is seen from FIG. 1 of plate 1 that the reflectance of each lock of hair treated with a composition according to the invention (compositions 1 to 4) is higher than that of the untreated hair, especially over the 500 to 760 nm section. The treated locks thus appear lighter.

Furthermore, the results show that the reflectance of the locks of hair of tone depth 2 treated with the compositions of the invention change very little after 10 shampoo washes (see FIG. 2, plate 1) or even 20 shampoo washes (see FIG. 3, plate 2). Thus, the colouring and the lightening effect on the hair remain virtually unchanged, which shows very good persistence with respect to shampooing of the dyes of the invention.

b-E) Combination with Blue Dye

Application Protocol:
Before Applying the Dyes, the Hair is Washed According to the Following Protocol:
Step 1: Application of Cleansing Shampoo (so as to Obtain Clean Hair):
1. Weigh out 0.4 ml of cleansing shampoo per gram of hair in a watch glass.
2. Wet the lock with tap water, passing the lock between the fingers for 5 seconds.
3. Drain the lock of hair dry between two fingers.
4. Apply the cleansing shampoo along the lock of hair (from the root to the end homogeneously).

5. Massage the lock gently between two fingers along its length (so as to work the shampoo into a lather) for 15 seconds from top to bottom (without making knots).
6. Rinse under tap water for 10 seconds, passing the lock between the fingers.
7. Drain the lock dry between two fingers.
8. Comb the lock.
9. Dry the lock with a hairdryer.

Protocol for Applying the Dyes of the Invention:

Step 2: Application of the Test Product of the Invention:
1. Prepare the solution of the dye compound of Example 1 at 0.5% w/w in water (solution A).
2. Place a 1 g lock in a channel.
3. Apply the solution of the test product along the lock of hair (from the root to the end homogeneously, BR=10).
4. Leave the composition to stand on the lock for 20 minutes on a hotplate at 37° C.
5. Rinse under tap water for 10 seconds, passing the lock between the fingers.
6. Drain the lock dry between two fingers.

The locks are then shampooed according to the following protocol, which may be repeated according to the number of shampoo washes performed:

Step 4: Application of Shampoo (Persistence):
1. Weigh out 0.4 ml of DOP camomile shampoo per gram of hair in a watch glass.
2. Wet the lock with tap water, passing the lock between the fingers for 5 seconds.
3. Drain the lock of hair dry between two fingers.
4. Apply the cleansing shampoo along the lock of hair (from the root to the end homogeneously).
5. Massage the lock gently between two fingers along its length (so as to work the shampoo into a lather) for 15 seconds from top to bottom (without making knots).
6. Rinse under tap water for 10 seconds, passing the lock between the fingers.
7. Drain the lock dry between two fingers.
8. Comb the lock.
9. Repeat steps 4 to 8 as many times as there are shampoo washes to be performed (1 to 10 shampoo washes).
10. Dry the lock under a hood.

Another application variant is to perform steps 1 and 2 and then to perform step 2' below, which makes it possible to combine a fluorescent dye and a blue direct dye in two successive steps.

Step 2': Application of the Blue Direct Dye Test Product
1. Prepare the solution of the blue direct dye at 0.5% w/w in water (solution A).
2. Place a 1 g lock in a channel.
3. Apply the solution of the test product along the lock of hair (from the root to the end homogeneously, bath ratio of 10).
4. Leave the composition to stand on the lock for 20 minutes on a hotplate at 37° C.
5. Rinse under tap water for 10 seconds, passing the lock between the fingers.
6. Drain the lock dry between two fingers.

Step 1 may be performed after step 2'. Steps 1 and 2' may also be performed in a single action. Another variant is to add 0.5% of blue direct dye to solution A and to follow step 2 above.

The colorimetric measurement of the lock is then taken using a Minolta 3610d spectrophotometer. (L, a, b system). The dyes are applied to locks of Caucasian hair NW 90%.

Combining Fluorescent Dye and Blue Direct Dye:

The blue direct dye is Basic Blue 124: (3-amino-7-(dimethylamino)-2-methoxyphenoxazin-5-ium) chloride, having the following structure:

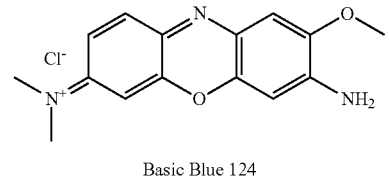

Basic Blue 124

(absorption wavelength $\lambda_{max}$=624 nm)

TABLE 3

| Product | pH | No. shampoo washes | L* (D65) | a* (D65) | b* (D65) | ΔE* (D65) |
|---|---|---|---|---|---|---|
| Basic Blue 124 | spontaneous | 1 | 18.89 | 0.73 | −10.13 | — |
| Basic Blue 124 + compound of Example 1 | 8.5 | 0 | 16.15 | 2.14 | −0.86 | 35.50 |
| Basic Blue 124 + compound of Example 1 | 8.5 | 5 | 16.30 | 1.45 | −2.48 | 35.94 |
| Basic Blue 124 + compound 1 | 8.5 | 10 | 16.71 | 1.26 | −2.98 | 35.74 |

It is seen visually that the colours obtained are very dark, very intense, aesthetic chestnut-browns—it was even possible to obtain black—this being achieved with only two dyes.

The colours derived from the mixture are also persistent especially with regard to successive shampoo washing, and significantly more intense than the colouring obtained with the blue dye alone (see Table 3).

The invention claimed is:
1. A process for dyeing and/or lightening human keratin fibres, comprising applying to said keratin fibres
a cosmetic composition comprising at least one direct dye selected from compounds of formula (I), (IIa), or (IIb) below:

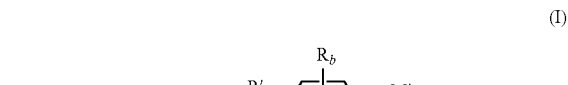

(I)

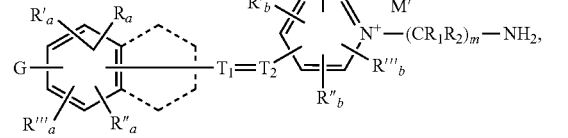

(IIa)

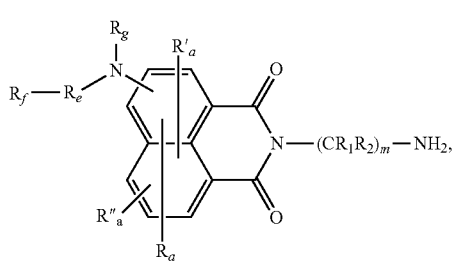

-continued

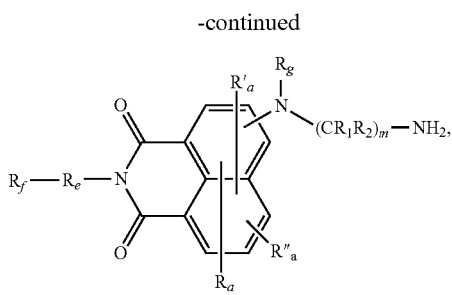

(IIb)

organic or mineral acid or base salts thereof, optical isomers, geometrical isomers and tautomers thereof, solvates thereof, or hydrates thereof;

wherein in formulas (I), (IIa), and (IIb):

$R_1$ and $R_2$, which may be identical or different, is a hydrogen atom or a $C_1$-$C_6$ alkyl group;

$T_1$ is a nitrogen atom or a group $C(R_i)$;

$T_2$ is a nitrogen atom or a group $C(R_{i'})$;

$R_a$, $R'_a$, $R''_a$, $R'''_a$, $R_b$, $R'_b$, $R''_b$, and $R'''_b$, which may be identical or different, is each independently selected from a) a hydrogen atom, b) a halogen atom, c) amino, d) $(C_1$-$C_4)$alkylamino, e) $(C_1$-$C_4)$dialkylamino, f) cyano, g) carboxy —C(O)OH or carboxylate —C(O)O$^-$, Q$^+$, h) hydroxy —OH or alkoxide —O$^-$Q$^+$, i) (poly)halo$(C_1$-$C_6)$alkyl, j) acylamino, k) $(C_1$-$C_6)$alkoxy, l) $(C_1$-$C_6)$alkylthio, m) (poly)hydroxy$(C_2$-$C_4)$alkoxy, n) $(C_1$-$C_6)$alkylcarbonyloxy, o) $(C_1$-$C_6)$alkoxycarbonyl, p) $(C_1$-$C_6)$alkylcarbonylamino, q) acylamino, r) carbamoyl, s) $(C_1$-$C_6)$alkylsulfonylamino, t) aminosulfonyl, u) —SO$_3$H or sulfonate —SO$_3^-$, Q$^+$, or v) $(C_1$-$C_6)$alkyl optionally substituted with a group selected from $(C_1$-$C_6)$alkoxy, hydroxyl, cyano, carboxyl, amino, (di)$(C_1$-$C_4)$alkylamino, or the two alkyl radicals borne by the nitrogen atom of the amino group form a 5- to 7-membered heterocycle optionally comprising another nitrogen or non-nitrogen heteroatom; or two groups $R_a$ and $R'_a$; $R_b$ and $R'_b$ borne by two adjacent carbon atoms together form a benzo or indeno ring, a fused heterocycloalkyl or fused heteroaryl group; the benzo, indeno, heterocycloalkyl, or heteroaryl ring being optionally substituted with a halogen atom, an amino group, $(C_1$-$C_4)$alkylamino group, $(C_1$-$C_4)$dialkylamino group, nitro group, cyano group, carboxyl group, hydroxyl group, trifluoromethyl group, an acylamino radical, $(C_1$-$C_4)$alkoxy (poly)hydroxy$(C_1$-$C_4)$alkoxy radical, $(C_1$-$C_4)$alkylcarbonyloxy radical, $(C_1$-$C_4)$alkoxycarbonyl radical, $(C_1$-$C_4)$alkylcarbonylamino radical, an acylamino radical, carbamoyl radical, alkoxyalkylsulfonylamino radical, an aminosulfonyl radical, or a $(C_1$-$C_6)$alkyl radical optionally substituted with: a group selected from $(C_1$-$C_6)$alkoxy, hydroxyl, cyano, carboxyl, amino, $(C_1$-$C_4)$alkylamino and $(C_1$-$C_4)$dialkylamino, or the two alkyl radicals borne by the nitrogen atom of the amino group form a 5- to 7-membered heterocycle optionally comprising another nitrogen or non-nitrogen heteroatom;

or when $T_1$ is $CR_i$, two groups $R_i$ and $R_a$; and/or when $T_2$ is a group, $R'_i$ and $R'_a$ together form a fused (hetero)cycloalkyl;

$R_g$ is selected from a hydrogen atom, a (hetero)aryl$(C_1$-$C_4)$alkyl group, or a $(C_1$-$C_6)$alkyl group that is optionally substituted;

$R_e$ is selected from a covalent bond, a linear or branched, optionally substituted $(C_1$-$C_8)$alkylene, or $(C_2$-$C_8)$alkenylene hydrocarbon-based chain;

$R_f$ is selected from a hydrogen atom, a $(C_1$-$C_4)$alkoxy group, an amino group $R_3R_4N$—, a quaternary ammonium group M', $R_3R_4R_5N^+$— wherein $R_3$, $R_4$ and $R_5$, which may be identical or different, is a hydrogen atom or a $(C_1$-$C_4)$ alkyl group or $R_3R_4N$—is an optionally substituted heteroaryl group, or M', $R_3R_4R_5N^+$— is an optionally substituted cationic heteroaryl group;

G is a group i) —NR$_c$R$_d$, ii) —OR with R selected from a) a hydrogen atom, b) an optionally substituted $(C_1$-$C_6)$alkyl group, c) an optionally substituted (hetero)aryl group, d) an optionally substituted (hetero)aryl$(C_1$-$C_6)$ alkyl group, e) optionally substituted (hetero)cycloalkyl group, or f) optionally substituted (hetero)cycloalkyl$(C_1$-$C_6)$alkyl group;

or when G is —NR$_c$R$_d$, two groups R$_c$ and R'$_a$ and/or R$_d$ and R$_a$ together form a saturated heteroaryl or heterocycle, optionally substituted with at least one $(C_1$-$C_6)$ alkyl groups;

$R_c$ and $R_d$, which may be identical or different, is a hydrogen atom or a group selected from a) optionally substituted (hetero)aryl, b) optionally substituted (hetero)aryl$(C_1$-$C_4)$alkyl, c) optionally substituted (hetero)cycloalkyl, d) optionally substituted (hetero)cycloalkyl $(C_1$-$C_4)$alkyl, or f) optionally substituted $(C_1$-$C_8)$alkyl;

or two adjacent radicals $R_c$ and $R_d$ borne by the same nitrogen atom together form an optionally substituted heterocyclic or optionally substituted heteroaryl group;

$R_i$ and $R'_i$, which may be identical or different, is a hydrogen atom or a $(C_1$-$C_4)$alkyl group;

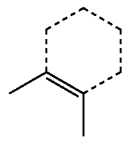

is a (hetero)aryl group fused to the phenyl ring; or is absent from the phenyl;

m is an integer between 1 and 18 inclusive;

M' is an anionic counterion, derived from a salt of an organic or mineral acid, or from an organic or mineral base that ensures the electrical neutrality of the molecule;

Q$^+$ is a cationic counterion, derived from a salt of an organic or mineral acid, or from an organic or mineral base that ensures the electrical neutrality of the molecule;

wherein when the molecule comprises a carboxylate, sulfonate, or alkoxide group, then M' and Q$^+$ are optionally absent to ensure the electrical neutrality of said molecule; and with the proviso that the compounds of formula (I) are not chosen from the following compound:

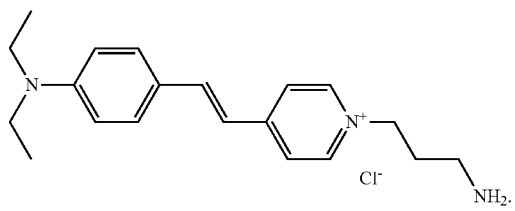 [SMILES: CCN(CC)c1ccc(/C=C/c2cc[n+](CCCN)cc2)cc1 ; [Cl-]]

2. The process according to claim 1, wherein the at least one direct dye of formula (I) is further selected from compounds of formula (I') below:

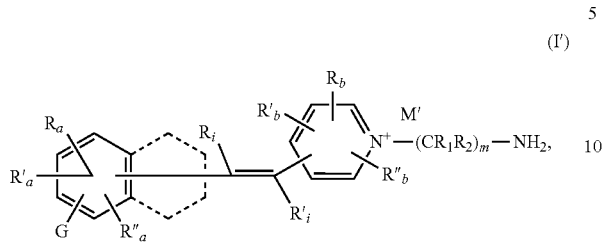

(I')

organic or mineral acid or base salts thereof, optical isomers thereof, geometrical isomers thereof, tautomers thereof, or solvates thereof
wherein;
- $R_1$ and $R_2$ are a hydrogen atom;
- $R_i$ and $R_{i'}$ are selected from a hydrogen atom or a $(C_1\text{-}C_4)$alkyl group;
- $R_a$, $R'_a$, and $R''_a$ are each independently selected from a hydrogen atom, a halogen atom, an —OH group, —O⁻Q⁺ group, $(C_1\text{-}C_6)$alkoxy group, nitro group, or cyano group;
- $R_b$, $R'_b$, and $R''_b$, which may be identical or different, are each independently selected from a hydrogen atom or a $(C_1\text{-}C_6)$alkyl group;
- or two contiguous radicals $R_b$ and $R'_b$ form, together with the carbon atoms that bear them, a benzo group that is fused to the pyridinium group, said benzo group optionally substituted;
- G is a group —$NR_cR_d$ or $(C_1\text{-}C_6)$alkoxy group which is optionally substituted;
- $R_i$ and $R'_i$, which may be identical or different, is a hydrogen atom or a $(C_1\text{-}C_4)$alkyl group;

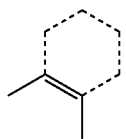

is an aryl or heteroaryl group fused to the phenyl ring; or is absent from the phenyl ring;
- m is an integer between 1 and 18 inclusive;
- $R_c$ and $R_d$, which may be identical or different, is a hydrogen atom, a $(C_1\text{-}C_8)$alkyl group optionally substituted with at least one groups selected from i) cyano, ii) $(C_1\text{-}C_3)$alkoxy, iii) hydroxyl, or iv) $(C_1\text{-}C_3)$alkylcarbonyl; and
- M' is an anionic counterion, derived from a salt of an organic or mineral acid, or from an organic or mineral base that ensures the electrical neutrality of the molecule;

wherein when the molecule comprises an alkoxide group, then M' and Q⁺ are optionally absent to ensure the electrical neutrality of said molecule.

3. The process according to claim 1, wherein the at least one direct dye of formula (I) is further selected from compounds of formula (I'') below:

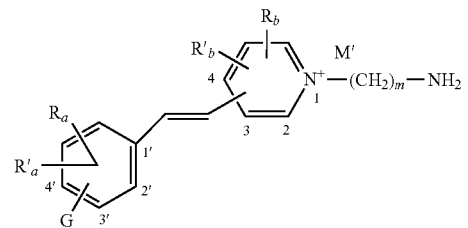

(I'')

organic or mineral acid salts thereof, optical isomers thereof, geometrical isomers thereof, tautomers thereof, solvates thereof, or hydrates thereof.

4. The process according to claim 3, wherein the cosmetic composition comprises at least one direct dye selected from compounds of formula (I'') with:
- the group G which is in the para position relative to the —CH═CH— group, i.e. in position 4' of the phenyl group, or in the ortho position, i.e. in position 2' of the phenyl; and/or
- the —CH═CH— group is in the para position of the pyridinium group, i.e. in position 4, or the —CH═CH— group is in the ortho position of the pyridinium group, i.e. in position 2.

5. The process according to claim 1, wherein the at least one direct dye of formula (I) is further selected from compounds of formula (I'''a) or (I'''b) below:

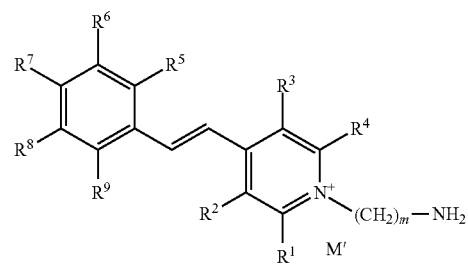

(I'''a)

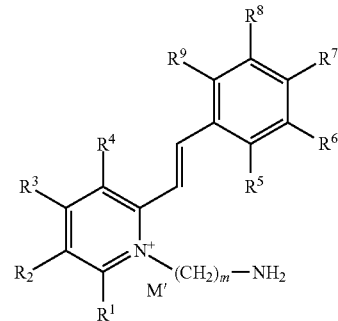

(I'''b)

organic or mineral acid salts thereof, optical isomers thereof, geometrical isomers thereof, tautomers thereof, solvates thereof, or hydrates thereof;
wherein formula (I'''a) or(I'''b):
- $R^1$, $R^2$, $R^3$, and $R^4$, which may be identical or different, is each independently selected from a hydrogen atom or a $(C_1\text{-}C_6)$alkyl group;
- $R^5$, $R^6$, $R^7$, $R^8$, and $R^9$, which may be identical or different, is each independently selected from i) a hydrogen atom, ii) a halogen atom, iii) a group OR, wherein R is a hydrogen atom or Q⁺, or a $(C_1\text{-}C_3)$alkyl group, iv) aryl group, v) aryl(C$_1$-C$_3$)alkyl group, vi) cyano group, vii) nitro group, viii) (C$_1$-C$_3$)alkylthio group, ix) amino NR$^{10}$R$^{11}$ group, wherein R$^{10}$ and R$^{11}$, which may be identical or different, is a) a hydrogen atom or b) a (C$_1$-C$_8$)alkyl group optionally substituted with at least one group selected from:

cyano, (C$_1$-C$_3$)alkoxy, hydroxyl, or (C$_1$-C$_3$)alkylcarbonyl;

m is an integer between 1 and 18 inclusive;

M' is an anionic counterion derived from salts of organic or mineral acids;

wherein when the molecule comprises an alkoxide group, then M' and Q$^+$ are optionally absent to ensure the electrical neutrality of said molecule.

6. The process according to claim 1, wherein the at least one direct dye of formula (I) is further selected from compounds of formula (I''''a) or (I''''b) below:

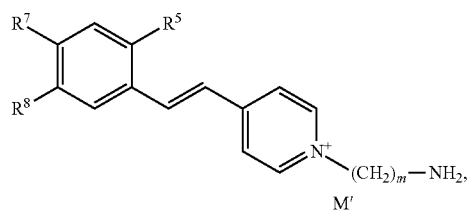

(I''''9a)

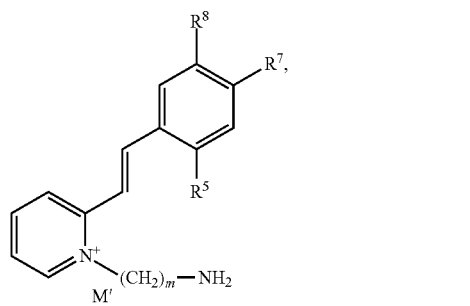

(I''''b)

wherein:

R$^5$ and R$^8$, which may be identical or different, is a hydrogen atom or a (C$_1$-C$_4$)alkoxy group;

R$^7$ is a (C$_1$-C$_4$)alkoxy or NR$^{10}$R$^{11}$ group, wherein R$^{10}$ and R$^{11}$, which may be identical or different, is a) a hydrogen atom, or b) a (C$_1$-C$_8$)alkyl group optionally substituted with at least one group selected from i) cyano, ii) (C$_1$-C$_3$)alkoxy, iii) hydroxyl, or iv) (C$_1$-C$_3$)alkylcarbonyl;

m is an integer between 1 and 18 inclusive; and

M' is an anionic counterion, derived from a salt of an organic or mineral acid, or from an organic or mineral base that ensures the electrical neutrality of the molecule.

7. The process according to claim 1, wherein the at least one direct dye of formula (IIa) is further selected from compounds of formula (II'a):

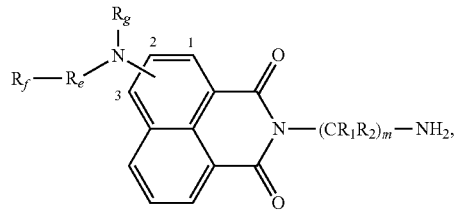

(II'a)

organic or mineral acid or base salts thereof, optical isomers thereof, geometrical isomers thereof, tautomers thereof, solvates thereof, or hydrates thereof; wherein the amino group R$_f$—R$_e$—N(R$_g$)— is on the carbon atom in position 3; wherein:

R$_1$ and R$_2$, which may be identical or different, is a hydrogen atom or a C$_1$-C$_6$ alkyl group;

R$_g$ is a (C$_1$-C$_4$)alkyl group or a hydrogen atom;

R$_e$ is an unsubstituted (C$_1$-C$_6$)alkylene group;

R$_f$ is a (di)(C$_1$-C$_4$)(alkyl)amino group; m is an integer between 1 and 16 inclusive.

8. The process according to claim 1, wherein the at least one direct dye of formula (I) is further selected from compounds of one of the following formulas:

formula (I'''a) wherein:

| R$^1$ | R$^2$ | R$^3$ | R$^4$ | R$^5$ | R$^6$ | R$^7$ | R$^8$ | R$^9$ | m |
|---|---|---|---|---|---|---|---|---|---|
| H | H | H | H | H | H | OCH$_3$ | OCH$_3$ | OCH$_3$ | 2 |
| H | H | H | H | OH | OCH$_3$ | H | H | H | 2 |
| H | H | H | H | H | H | H | H | H | 2 |
| H | H | H | H | H | OCH$_3$ | OCH$_3$ | H | H | 2 |
| H | H | H | H | OH | H | OH | H | H | 6 |
| H | H | H | H | OCH$_3$ | H | OCH$_3$ | OCH$_3$ | H | 6 |
| H | H | H | H | H | H | OH | H | H | 6 |
| H | H | H | H | OCH$_3$ | H | H | H | F | 2 |
| H | H | H | H | H | H | C(O)—OH | H | H | 2 |
| H | H | H | H | H | H | Isopropyl | H | H | 2 |
| H | H | H | H | H | H | N(CH$_2$CH$_2$C(O)CH$_3$)$_2$ | H | H | 2 |
| H | H | H | H | OH | H | OCH$_3$ | H | H | 2 |
| H | H | H | H | H | H | OH | H | H | 2 |
| H | H | H | H | H | OCH$_3$ | OH | OH | H | 2 |
| H | H | H | H | H | CH$_3$ | OCH$_2$Ph | CH$_3$ | H | 2 |
| H | H | H | H | H | OCH$_3$ | OCH$_3$ | OCH$_3$ | H | 2 |
| H | H | H | H | H | OCH$_3$ | OCH$_3$ | OCH$_3$ | H | 6 |
| H | H | H | H | H | H | N(CH$_3$)$_2$ | H | H | 6 |
| H | H | H | H | H | H | OCH$_3$ | OCH$_3$ | OCH$_3$ | 6 |
| H | H | H | H | H | H | Phenyl | H | H | 6 |
| H | H | H | H | H | OCH$_3$ | OCH$_3$ | H | H | 6 |
| H | H | H | H | H | H | C(O)—OH | H | H | 6 |
| H | H | H | H | H | H | N(n-Butyl)$_2$ | H | H | 2 |
| H | H | H | H | H | H | OCH$_3$ | OCH$_3$ | H | 3 |
| H | H | H | H | H | H | OCH$_3$ | OCH$_3$ | H | 2 |
| H | H | H | H | H | H | OCH$_3$ | OCH$_3$ | H | 5 |
| H | H | H | H | H | H | OCH$_3$ | H | H | 3 |
| H | H | H | H | H | H | N(CH$_3$)$_2$ | H | H | 3 |
| H | H | H | H | H | H | H | H | H | 3 | organic or mineral acid or base salts thereof, optical isomers thereof, geometrical isomers thereof, tautomers thereof, solvates thereof, or hydrates thereof;

formula (I'''b), wherein:

| R¹  | R² | R³ | R⁴ | R⁵   | R⁶   | R⁷                                   | R⁸        | R⁹   | m |
|-----|----|----|----|------|------|--------------------------------------|-----------|------|---|
| CH₃ | H  | H  | H  | OH   | H    | OCH₃                                 | H         | H    | 2 |
| CH₃ | H  | H  | H  | H    | H    | OCH₃                                 | OCH₂—Ph   | H    | 2 |
| CH₃ | H  | H  | H  | H    | H    | H                                    | H         | OCH₃ | 2 |
| CH₃ | H  | H  | H  | F    | H    | H                                    | H         | H    | 2 |
| CH₃ | H  | H  | H  | H    | H    | H                                    | OPh       | H    | 2 |
| CH₃ | H  | H  | H  | H    | H    | N(CH₂CH₂OAc)₂                        | H         | H    | 2 |
| CH₃ | H  | H  | H  | OCH₃ | H    | OCH₃                                 | OCH₃      | H    | 2 |
| CH₃ | H  | H  | H  | H    | H    | H                                    | CH₃       | H    | 2 |
| CH₃ | H  | H  | H  | H    | H    | OH                                   | H         | H    | 2 |
| CH₃ | H  | H  | H  | H    | OCH₃ | OCH₃                                 | OCH₃      | H    | 2 |
| CH₃ | H  | H  | H  | H    | OCH₃ | OH                                   | OH        | H    | 2 |
| CH₃ | H  | H  | H  | H    | H    | OCH₃                                 | OCH₃      | OCH₃ | 2 |
| CH₃ | H  | H  | H  | H    | H    | H                                    | OCH₃      | OH   | 2 |
| CH₃ | H  | H  | H  | H    | H    | N(n-butyl)₂                          | H         | H    | 2 |
| CH₃ | H  | H  | H  | H    | OCH₃ | OCH₃                                 | H         | H    | 2 |
| CH₃ | H  | H  | H  | H    | H    | H                                    | H         | H    | 2 |
| CH₃ | H  | H  | H  | H    | H    | i-propyl                             | H         | H    | 2 |
| H   | H  | H  | H  | H    | H    | OH                                   | H         | H    | 6 |
| H   | H  | H  | H  | H    | OCH₃ | OCH₃                                 | OCH₃      | H    | 6 |
| H   | H  | H  | H  | OH   | H    | OCH₃                                 | H         | H    | 2 |
| H   | H  | H  | H  | OCH₃ | H    | H                                    | OCH₃      | OCH₃ | 2 |
| H   | H  | H  | H  | H    | H    | H                                    | H         | Br   | 2 |
| H   | H  | H  | H  | H    | H    | OH                                   | H         | H    | 2 |
| H   | H  | H  | H  | H    | H    | N(CH₃)₂                              | H         | H    | 6 |
| H   | H  | H  | H  | OCH₃ | OCH₃ | OCH₃                                 | H         | H    | 6 |
| H   | H  | H  | H  | OH   | OCH₃ | H                                    | H         | H    | 6 |
| H   | H  | H  | H  | H    | OCH₃ | OCH₃                                 | H         | H    | 6 |
| H   | H  | H  | H  | H    | OCH₃ | OCH₃                                 | H         | H    | 2 |
| H   | H  | H  | H  | H    | H    | C(O)—OH                              | H         | H    | 6 |
| H   | H  | H  | H  | H    | H    | C(O)—OH                              | H         | H    | 2 |
| H   | H  | H  | H  | H    | H    | i-propyl                             | H         | H    | 2 |
| H   | H  | H  | H  | H    | H    | N(CH₃)CH₂CH₂CN                       | H         | H    | 2 |
| H   | H  | H  | H  | H    | H    | OCH₃                                 | OCH₂Ph    | H    | 2 |
| H   | H  | H  | H  | H    | H    | H                                    | OPh       | H    | 2 |
| H   | H  | H  | H  | H    | H    | N(CH₂CH₂C(O)CH₃)₂                    | H         | H    | 2 |
| H   | H  | H  | H  | OH   | H    | OCH₃                                 | H         | H    | 6 |
| H   | H  | H  | H  | H    | OCH₃ | OCH₃                                 | OCH₃      | H    | 2 |
| H   | H  | H  | H  | OCH₃ | H    | OCH₃                                 | OCH₃      | H    | 6 |
| H   | H  | H  | H  | H    | H    | H                                    | CH₃       | H    | 2 |
| H   | H  | H  | H  | H    | H    | N(CH₃)CH₂CH₂OH                       | H         | H    | 2 |
| CH₃ | H  | H  | H  | H    | H    | N(CH₃)₂                              | H         | H    | 2 | organic or mineral acid or base salts thereof, geometrical isomers thereof, tautomers thereof, solvates thereof, or hydrates thereof;

formulas (I''''a) and (I''''b), wherein:

| R⁵ | R⁷              | R⁸ | m  |
|----|-----------------|----|----|
| H  | N(CH₂CH₂OH)₂    | H  | 2  |
| H  | N(CH₂CH₂OH)₂    | H  | 3  |
| H  | N(CH₂CH₂OH)₂    | H  | 4  |
| H  | N(CH₂CH₂OH)₂    | H  | 5  |
| H  | N(CH₂CH₂OH)₂    | H  | 6  |
| H  | N(CH₂CH₂OH)₂    | H  | 8  |
| H  | N(CH₂CH₂OH)₂    | H  | 10 |
| H  | N(CH₂CH₂OH)₂    | H  | 12 |
| H  | N(CH₂CH₂OH)₂    | H  | 14 |
| H  | N(CH₂CH₂OH)₂    | H  | 16 | and

| R⁵   | R⁷   | R⁸   | M  |
|------|------|------|----|
| OCH₃ | OCH₃ | OCH₃ | 2  |
| OCH₃ | OCH₃ | OCH₃ | 3  |
| OCH₃ | OCH₃ | OCH₃ | 3  |
| OCH₃ | OCH₃ | OCH₃ | 4  |
| OCH₃ | OCH₃ | OCH₃ | 5  |
| OCH₃ | OCH₃ | OCH₃ | 8  |
| OCH₃ | OCH₃ | OCH₃ | 10 |
| OCH₃ | OCH₃ | OCH₃ | 12 |
| OCH₃ | OCH₃ | OCH₃ | 14 |
| OCH₃ | OCH₃ | OCH₃ | 16 | organic or mineral acid or base salts thereof, geometrical isomers thereof, tautomers thereof, solvates thereof, or hydrates thereof;

or

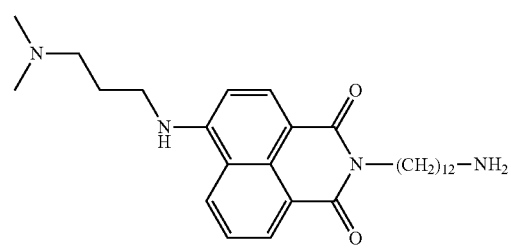

organic or mineral acid salts thereof, solvates thereof, or hydrates thereof.

9. The process according to claim 1, wherein the cosmetic composition is applied to light keratin fibres.

10. The process according to claim 9, comprising i) applying to said keratin materials a cosmetic composition which comprises at least one direct dye of formula (I), (IIa), or (IIb); and ii) applying a cosmetic composition which comprises at least one blue dye; wherein steps i) and ii) are performed together or separately.

11. The process according to claim 10, wherein the process does not use any dyes other than at least one direct dye of formula (I), (IIa), or (IIb) and at least one blue dye.

12. The process according to claim 1, wherein the cosmetic composition is applied to dark keratin fibres; wherein the at least one dye of formula (I) is further selected from those of formulas (I'), (I''), (I'''a), (I'''b), (I''''a), (I''''b), (IIa), (IIb), or mixtures thereof.

13. The process according to claim 1, wherein the process does not use any reducing agent.

14. The process according to claim 1, wherein the process does not use any chemical oxidizing agent.

15. A compound selected from compounds of formula (I''''a) or (I''''b) below:

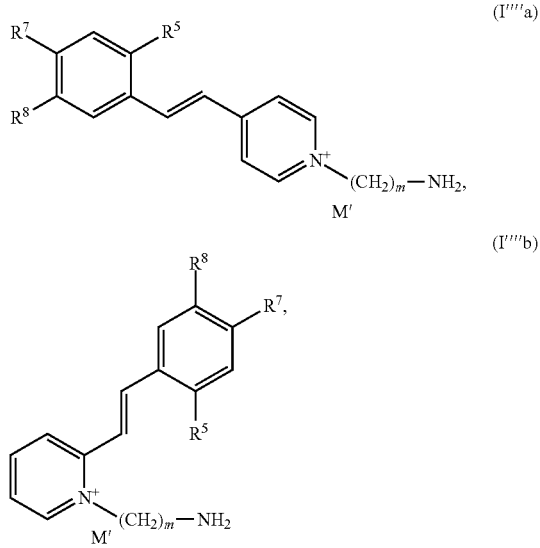

wherein:
- $R^5$ and $R^8$, which may be identical or different, is a hydrogen atom or a $(C_1-C_4)$alkoxy group;
- $R^7$ is a $(C_1-C_4)$alkoxy or $NR^{10}R^{11}$ group, wherein $R^{10}$ and $R^{11}$, which may be identical or different, is a) a hydrogen atom, or b) a $(C_1-C_8)$alkyl group optionally substituted with at least one group selected from i) cyano, ii) $(C_1-C_3)$alkoxy, iii) hydroxyl, or iv) $(C_1-C_3)$alkylcarbonyl;
- m is an integer between 1 and 18 inclusive; and
- M' is an anionic counterion, derived from a salt of an organic or mineral acid, or from an organic or mineral base that ensures the electrical neutrality of the molecule;
  wherein the compound of formula (I''''a) is different from the following compound:

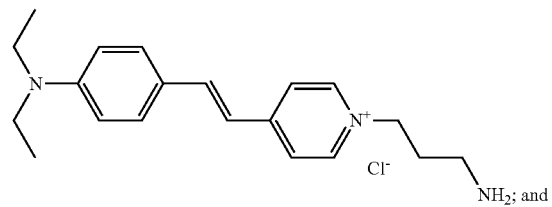

wherein in the compound of formula (I''''a), when $R^5$ and $R^8$ are hydrogen, R7 is an $NR^{10}R^{11}$ group, and $R^{10}$ or $R^{11}$ is an alkyl group, then at least one of $R^{10}$ and $R^{11}$ is substituted.

16. A cosmetic composition comprising at least one direct dye selected from compounds of formula (I), (IIa), or (IIb) below:

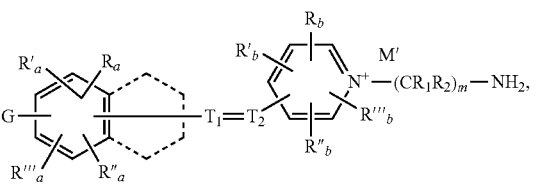

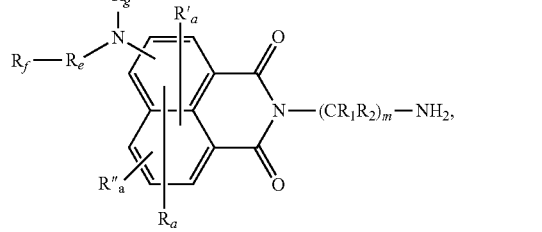

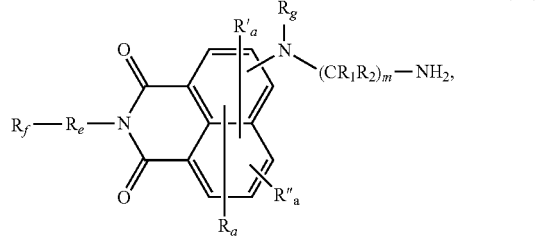

organic or mineral acid or base salts thereof, optical isomers thereof, geometrical isomers thereof, tautomers thereof, solvates thereof, or hydrates thereof;
wherein in formulas (I), (IIa), and (IIb):
- $R_1$ and $R_2$, which may be identical or different, is a hydrogen atom or a $C_1-C_6$ alkyl group;
- $T_1$ is a nitrogen atom or a group $C(R_i)$;
- $T_2$ is a nitrogen atom or a group $C(R_j)$;
- $R_a$, $R'_a$, $R''_a$, $R'''_a$, $R_b$, $R'_b$, $R''_b$, and $R'''_b$, which may be identical or different, is each independently selected from a) a hydrogen atom, b) a halogen atom, c) amino, d) $(C_1-C_4)$alkylamino, e) $(C_1-C_4)$dialkylamino, f) cyano, g) carboxy —C(O)OH or carboxylate —C(O)O⁻, Q⁺, h) hydroxy —OH or alkoxide —O⁻Q⁺, i) (poly)halo$(C_1-C_6)$alkyl, j) acylamino, k) $(C_1-C_6)$alkoxy, l) $(C_1-C_6)$alkylthio, m) (poly)hydroxy$(C_2-C_4)$alkoxy, n) $(C_1-C_6)$alkylcarbonyloxy, o) $(C_1-C_6)$alkoxycarbonyl, p) $(C_1-C_6)$alkylcarbonylamino, q) acylamino, r) carbamoyl, s) ($C_1$-$C_6$) alkylsulfonylamino, t) aminosulfonyl, u) —$SO_3H$ or sulfonate —$SO_3^-$, $Q^+$, or v) ($C_1$-$C_6$)alkyl optionally substituted with a group selected from ($C_1$-$C_6$) alkoxy, hydroxyl, cyano, carboxyl, amino, (di)($C_1$-$C_4$)alkylamino, or the two alkyl radicals borne by the nitrogen atom of the amino group form a 5- to 7-membered heterocycle optionally comprising another nitrogen or non-nitrogen heteroatom; or two groups $R_a$ and $R'_a$; $R_b$ and $R'_b$ borne by two adjacent carbon atoms together form a benzo or indeno ring, a fused heterocycloalkyl or fused heteroaryl group; the benzo, indeno, heterocycloalkyl, or heteroaryl ring being optionally substituted with a halogen atom, an amino group, ($C_1$-$C_4$)alkylamino group, ($C_1$-$C_4$)dialkylamino group, nitro group, cyano group, carboxyl group, hydroxyl group, trifluoromethyl group, an acylamino radical, ($C_1$-$C_4$)alkoxy (poly)hydroxy($C_1$-$C_4$)alkoxy radical, ($C_1$-$C_4$)alkylcarbonyloxy radical, ($C_1$-$C_4$)alkoxycarbonyl radical, ($C_1$-$C_4$)alkylcarbonylamino radical, an acylamino radical, carbamoyl radical, alkoxyalkylsulfonylamino radical, an aminosulfonyl radical, or a ($C_1$-$C_6$)alkyl radical optionally substituted with: a group selected from ($C_1$-$C_6$)alkoxy, hydroxyl, cyano, carboxyl, amino, ($C_1$-$C_4$)alkylamino and ($C_1$-$C_4$)dialkylamino, or the two alkyl radicals borne by the nitrogen atom of the amino group form a 5- to 7-membered heterocycle optionally comprising another nitrogen or non-nitrogen heteroatom;

or when $T_1$ is $CR_i$, two groups $R_i$ and $R_a$; and/or when $T_2$ is a group, $R'_i$ and $R'_a$ together form a fused (hetero)cycloalkyl;

$R_g$ is selected from a hydrogen atom, a (hetero)aryl($C_1$-$C_4$)alkyl group, or a ($C_1$-$C_6$)alkyl group that is optionally substituted;

$R_e$ is selected from a covalent bond, a linear or branched, optionally substituted ($C_1$-$C_8$)alkylene, or ($C_2$-$C_8$)alkenylene hydrocarbon-based chain;

$R_f$ is selected from a hydrogen atom, a ($C_1$-$C_4$)alkoxy group, an amino group $R_3R_4N$—, a quaternary ammonium group M', $R_3R_4R_5N^+$— wherein $R_3$, $R_4$ and $R_5$, which may be identical or different, is a hydrogen atom or a ($C_1$-$C_4$) alkyl group or $R_3R_4N$-is an optionally substituted heteroaryl group, or M', $R_3R_4R_5N^+$— is an optionally substituted cationic heteroaryl group;

G is a group i) —$NR_cR_d$, ii) —OR with R selected from a) a hydrogen atom, b) an optionally substituted ($C_1$-$C_6$)alkyl group, c) an optionally substituted (hetero)aryl group, d) an optionally substituted (hetero)aryl($C_1$-$C_6$)alkyl group, e) optionally substituted (hetero)cycloalkyl group, or f) optionally substituted (hetero)cycloalkyl($C_1$-$C_6$)alkyl group;

or when G is —$NR_cR_d$, two groups $R_c$ and $R'_a$ and/or $R_d$ and $R_a$ together form a saturated heteroaryl or heterocycle, optionally substituted with at least one ($C_1$-$C_6$)alkyl groups;

$R_c$ and $R_d$, which may be identical or different, is a hydrogen atom or a group selected from a) optionally substituted (hetero)aryl, b) optionally substituted (hetero)aryl($C_1$-$C_4$)alkyl, c) optionally substituted (hetero)cycloalkyl, d) optionally substituted (hetero) cycloalkyl($C_1$-$C_4$)alkyl, or f) optionally substituted ($C_1$-$C_8$)alkyl;

or two adjacent radicals $R_c$ and $R_d$ borne by the same nitrogen atom together form an optionally substituted heterocyclic or optionally substituted heteroaryl group;

$R_i$ and $R'_i$, which may be identical or different, is a hydrogen atom or a ($C_1$-$C_4$)alkyl group;

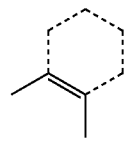

is a (hetero)aryl group fused to the phenyl ring; or is absent from the phenyl;

m is an integer between 1 and 18 inclusive;

M' is an anionic counterion, derived from a salt of an organic or mineral acid, or from an organic or mineral base that ensures the electrical neutrality of the molecule;

$Q^+$ is a cationic counterion, derived from a salt of an organic or mineral acid, or from an organic or mineral base that ensures the electrical neutrality of the molecule;

wherein when the molecule comprises a carboxylate, sulfonate, or alkoxide group, then M' and $Q^+$ are optionally absent to ensure the electrical neutrality of said molecule;

and at least one blue dye.

17. A cosmetic composition comprising at least one compound selected from compounds of formula (I''''a) or (I''''b) below:

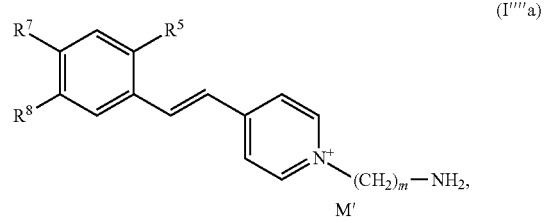

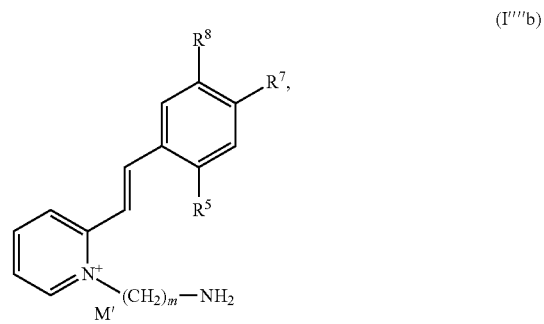

wherein:

$R^5$ and $R^8$, which may be identical or different, is a hydrogen atom or a ($C_1$-$C_4$)alkoxy group;

$R^7$ is a ($C_1$-$C_4$)alkoxy or $NR^{10}R^{11}$ group, wherein $R^{10}$ and $R^{11}$, which may be identical or different, is a) a hydrogen atom, or b) a ($C_1$-$C_8$)alkyl group optionally substituted with at least one group selected from i) cyano, ii) ($C_1$-$C_3$)alkoxy, iii) hydroxyl, or iv) ($C_1$-$C_3$)alkylcarbonyl;

m is an integer between 1 and 18 inclusive; and
M' is an anionic counterion, derived from a salt of an organic or mineral acid, or from an organic or mineral base that ensures the electrical neutrality of the molecule;

wherein the compound of formula (I''''a) is different from the following compound:

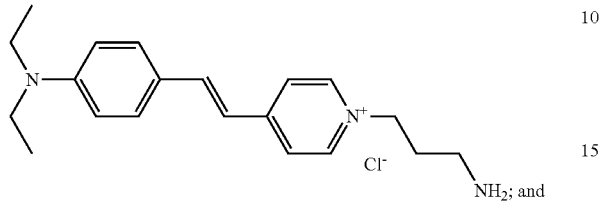

wherein in the compound of formula (I''''a), when $R^5$ and $R^8$ are hydrogen, $R_7$ is an $NR^{10}R^{11}$ group, and $R^{10}$ or $R^{11}$ is an alkyl group, then at least one of $R^{10}$ and $R^{11}$ is substituted.

* * * * *